United States Patent
Causevic et al.

(10) Patent No.: US 11,331,004 B2
(45) Date of Patent: May 17, 2022

(54) SAMPLING AND STORAGE REGISTRY DEVICE FOR BREATH GAS ANALYSIS

(71) Applicant: Capnia, Inc., Foster City, CA (US)

(72) Inventors: Elvir Causevic, San Francisco, CA (US); Anthony D. Wondka, San Ramon, CA (US); Anish Bhatnagar, Redwood City, CA (US)

(73) Assignee: CAPNIA, INC., Foster City, CA (US)

( * ) Notice: Subject to any disclaimer, the term of this patent is extended or adjusted under 35 U.S.C. 154(b) by 484 days.

(21) Appl. No.: 15/897,606

(22) Filed: Feb. 15, 2018

(65) Prior Publication Data

US 2019/0021632 A1    Jan. 24, 2019

Related U.S. Application Data

(63) Continuation of application No. 14/179,381, filed on Feb. 12, 2014, now abandoned.

(60) Provisional application No. 61/794,254, filed on Mar. 15, 2013, provisional application No. 61/763,896, filed on Feb. 12, 2013.

(51) Int. Cl.
*A61B 5/083* (2006.01)
*A61B 5/087* (2006.01)
*A61B 5/097* (2006.01)
*A61B 5/00* (2006.01)
*A61B 5/091* (2006.01)

(52) U.S. Cl.
CPC .............. *A61B 5/083* (2013.01); *A61B 5/087* (2013.01); *A61B 5/097* (2013.01); *A61B 5/4836* (2013.01); *A61B 5/0833* (2013.01); *A61B 5/0873* (2013.01); *A61B 5/091* (2013.01)

(58) Field of Classification Search
CPC .............. A61B 5/083–0836; A61B 5/087–097
See application file for complete search history.

(56) References Cited

U.S. PATENT DOCUMENTS

| | | | |
|---|---|---|---|
| 2,073,192 A | 3/1937 | Connell | |
| 3,306,283 A | 2/1967 | Arp | |
| 3,343,529 A | 9/1967 | Miller et al. | |
| 3,858,573 A | 1/1975 | Ryan et al. | |
| (Continued) | | | |

FOREIGN PATENT DOCUMENTS

| | | |
|---|---|---|
| CN | 1097120 A | 1/1995 |
| CN | 1767785 A | 5/2006 |
| (Continued) | | |

OTHER PUBLICATIONS

Bartlett, R.G. et al. (1957). "Maximum breathing capacity with various expiratory and inspiratory resistances (single and combined) at various breathing rates," *J. Appl. Physiol.* 11 (1):79-83.

(Continued)

*Primary Examiner* — Daniel L Cerioni
*Assistant Examiner* — Raymond P Dulman
(74) *Attorney, Agent, or Firm* — Cooley LLP

(57) ABSTRACT

Methods and systems are described to obtain and analyze one or more gas samples from the breath of a person, and organizing the samples in a sample registry for subsequent analysis. This technique solves the various problems that are associated with targeting an individual breath for analysis, and allows for additional versatility and options in the analysis process.

6 Claims, 14 Drawing Sheets

(56) References Cited

U.S. PATENT DOCUMENTS

| | | | |
|---|---|---|---|
| 3,910,261 A | 10/1975 | Ragsdale et al. | |
| 3,923,043 A | 12/1975 | Yanda | |
| 4,440,177 A | 4/1984 | Anderson et al. | |
| 4,619,269 A | 10/1986 | Cutler et al. | |
| 4,671,298 A | 6/1987 | Babb et al. | |
| 5,003,985 A | 4/1991 | White et al. | |
| 5,050,615 A * | 9/1991 | Malkamaki | A61B 5/0836 600/532 |
| 5,069,220 A | 12/1991 | Casparie et al. | |
| 5,072,737 A | 12/1991 | Goulding | |
| 5,129,401 A | 7/1992 | Corenman et al. | |
| 5,285,794 A | 2/1994 | Lynch | |
| 5,293,875 A | 3/1994 | Stone | |
| 5,357,971 A | 10/1994 | Sheehan et al. | |
| 5,361,771 A | 11/1994 | Craine et al. | |
| 5,361,772 A | 11/1994 | Murnick et al. | |
| 5,363,857 A | 11/1994 | Howard | |
| 5,383,469 A | 1/1995 | Vreman et al. | |
| 5,474,062 A | 12/1995 | DeVries et al. | |
| 5,533,512 A | 7/1996 | Novotny et al. | |
| 5,533,513 A | 7/1996 | Ueda et al. | |
| 5,573,005 A | 11/1996 | Ueda et al. | |
| 5,787,885 A | 8/1998 | Lemelson | |
| 5,924,995 A | 7/1999 | Klein et al. | |
| 5,971,934 A | 10/1999 | Scherer et al. | |
| 6,010,459 A | 1/2000 | Silkoff et al. | |
| 6,038,913 A | 3/2000 | Gustafsson et al. | |
| 6,251,082 B1 | 6/2001 | Rayburn | |
| 6,278,975 B1 | 8/2001 | Brant et al. | |
| 6,428,483 B1 | 8/2002 | Carlebach | |
| 6,544,190 B1 | 4/2003 | Smits et al. | |
| 6,582,376 B2 | 6/2003 | Baghdassarian | |
| 6,620,107 B2 | 9/2003 | Payne et al. | |
| 6,733,463 B2 | 5/2004 | Moilanen et al. | |
| 6,739,335 B1 | 5/2004 | Rapport et al. | |
| 6,799,575 B1 | 10/2004 | Carter | |
| 6,884,222 B1 * | 4/2005 | Braig | A61B 5/083 600/529 |
| 7,063,667 B1 | 6/2006 | Ben-Oren et al. | |
| 7,076,371 B2 | 7/2006 | Fu | |
| 7,191,000 B2 | 3/2007 | Zhu et al. | |
| 7,192,782 B2 | 3/2007 | Roller et al. | |
| 7,223,244 B1 | 5/2007 | Koh | |
| 7,600,439 B1 | 10/2009 | Patterson et al. | |
| 7,775,210 B2 | 8/2010 | Schobel et al. | |
| 7,814,906 B2 | 10/2010 | Moretti | |
| 8,021,308 B2 | 9/2011 | Carlson et al. | |
| 8,251,914 B2 | 8/2012 | Daniels et al. | |
| 8,485,984 B2 | 7/2013 | Giron et al. | |
| 8,672,852 B2 | 3/2014 | Gavish | |
| 8,679,029 B2 | 3/2014 | Krauss et al. | |
| 9,095,534 B2 | 8/2015 | Stenzler et al. | |
| 9,541,497 B2 | 1/2017 | Heyne et al. | |
| 9,655,543 B2 | 5/2017 | Aoki et al. | |
| 10,034,621 B2 | 7/2018 | Wondka et al. | |
| 10,499,819 B2 | 12/2019 | Wondka et al. | |
| 11,058,324 B2 | 7/2021 | Wondka et al. | |
| 2001/0037070 A1 | 11/2001 | Cranley et al. | |
| 2002/0005197 A1 | 1/2002 | DeVries et al. | |
| 2002/0095096 A1 * | 7/2002 | Mault | A61B 5/029 600/531 |
| 2002/0138213 A1 | 9/2002 | Mault | |
| 2002/0151814 A1 | 10/2002 | Payne et al. | |
| 2003/0008407 A1 | 1/2003 | Fu | |
| 2003/0109795 A1 | 6/2003 | Webber | |
| 2003/0134427 A1 | 7/2003 | Roller et al. | |
| 2003/0191405 A1 | 10/2003 | Rich et al. | |
| 2003/0208133 A1 | 11/2003 | Mault | |
| 2003/0216660 A1 | 11/2003 | Ben-Oren et al. | |
| 2004/0077995 A1 | 4/2004 | Ferek-Petric et al. | |
| 2004/0210154 A1 | 10/2004 | Kline | |
| 2005/0137491 A1 | 6/2005 | Paz et al. | |
| 2005/0153346 A1 * | 7/2005 | Schneider | G01N 27/44717 435/6.12 |
| 2005/0177056 A1 | 8/2005 | Giron et al. | |
| 2006/0094964 A1 | 5/2006 | Ragauskas et al. | |
| 2006/0133960 A1 | 6/2006 | Ahmad | |
| 2006/0178592 A1 | 8/2006 | Nason et al. | |
| 2006/0195040 A1 | 8/2006 | Nason et al. | |
| 2006/0200037 A1 | 9/2006 | Falasco | |
| 2006/0241507 A1 | 10/2006 | Carlson et al. | |
| 2006/0253045 A1 | 11/2006 | Coifman | |
| 2007/0016092 A1 | 1/2007 | Shaw et al. | |
| 2007/0073182 A1 | 3/2007 | Wilson | |
| 2007/0129647 A1 | 6/2007 | Lynn | |
| 2007/0144518 A1 | 6/2007 | Acker et al. | |
| 2007/0155208 A1 | 7/2007 | Pirzada | |
| 2007/0167853 A1 | 7/2007 | Melker et al. | |
| 2007/0173731 A1 | 7/2007 | Meka et al. | |
| 2007/0179395 A1 | 8/2007 | Sotos et al. | |
| 2007/0213620 A1 | 9/2007 | Reisfeld | |
| 2007/0213624 A1 | 9/2007 | Reisfeld et al. | |
| 2007/0232950 A1 * | 10/2007 | West | A61B 5/083 600/532 |
| 2007/0261472 A1 | 11/2007 | Flaherty et al. | |
| 2008/0009762 A1 | 1/2008 | Hampton et al. | |
| 2008/0038154 A1 | 2/2008 | Longbottom et al. | |
| 2008/0119753 A1 | 5/2008 | Ricciardelli et al. | |
| 2008/0119754 A1 | 5/2008 | Hietala | |
| 2008/0121230 A1 | 5/2008 | Cortez et al. | |
| 2008/0221471 A1 | 9/2008 | Djupesland et al. | |
| 2008/0289628 A1 * | 11/2008 | Hallback | A61M 16/0051 128/203.12 |
| 2009/0044805 A1 | 2/2009 | Somaiya et al. | |
| 2009/0054799 A1 | 2/2009 | Vrtis et al. | |
| 2009/0187113 A1 | 7/2009 | Friedman et al. | |
| 2009/0246891 A1 | 10/2009 | Sato et al. | |
| 2009/0247891 A1 | 10/2009 | Wood | |
| 2010/0268106 A1 | 10/2010 | Johnson et al. | |
| 2010/0317986 A1 | 12/2010 | Colman et al. | |
| 2011/0004108 A1 | 1/2011 | Peyton | |
| 2011/0021942 A1 | 1/2011 | Choe et al. | |
| 2011/0066060 A1 | 3/2011 | von Bahr et al. | |
| 2011/0196295 A1 | 8/2011 | Gonzalez et al. | |
| 2011/0257550 A1 | 10/2011 | Choi | |
| 2011/0263947 A1 | 10/2011 | Utley et al. | |
| 2012/0055481 A1 | 3/2012 | Orr et al. | |
| 2012/0090378 A1 | 4/2012 | Wang et al. | |
| 2012/0101400 A1 * | 4/2012 | Kurosawa | A61B 5/038 600/533 |
| 2012/0215125 A1 | 8/2012 | Orr et al. | |
| 2012/0247471 A1 | 10/2012 | Masic et al. | |
| 2012/0302908 A1 | 11/2012 | Hemnes et al. | |
| 2012/0310104 A1 | 12/2012 | Van Kesteren et al. | |
| 2013/0217029 A1 | 8/2013 | Sislian et al. | |
| 2013/0253360 A1 * | 9/2013 | Wang | G01N 33/0047 600/532 |
| 2013/0267862 A1 | 10/2013 | Jaffe et al. | |
| 2013/0331723 A1 | 12/2013 | Hernandez-Silveira et al. | |
| 2014/0228699 A1 | 8/2014 | Causevic | |
| 2014/0275857 A1 | 9/2014 | Toth et al. | |
| 2015/0065900 A1 | 3/2015 | Wondka et al. | |
| 2015/0065901 A1 | 3/2015 | Bhatnagar et al. | |
| 2015/0265184 A1 | 9/2015 | Wondka et al. | |
| 2016/0106343 A1 | 4/2016 | Wondka et al. | |
| 2019/0029547 A1 | 1/2019 | Watarai et al. | |
| 2019/0142303 A1 | 5/2019 | Wondka et al. | |
| 2019/0175067 A1 | 6/2019 | Wondka et al. | |
| 2020/0046254 A1 | 2/2020 | Wondka et al. | |
| 2020/0305729 A1 | 10/2020 | Wondka et al. | |

FOREIGN PATENT DOCUMENTS

| | | |
|---|---|---|
| CN | 1895691 A | 1/2007 |
| CN | 1926427 A | 3/2007 |
| CN | 1950120 A | 4/2007 |
| CN | 101026995 A | 8/2007 |
| CN | 101098726 A | 1/2008 |
| CN | 101153840 A | 4/2008 |
| CN | 101214151 A | 7/2008 |
| CN | 101340941 A | 1/2009 |
| CN | 101366672 A | 2/2009 |
| CN | 101547716 A | 9/2009 |

(56) References Cited

FOREIGN PATENT DOCUMENTS

| | | |
|---|---|---|
| CN | 101636109 A | 1/2010 |
| CN | 101657710 A | 2/2010 |
| CN | 201692453 U | 1/2011 |
| CN | 201727541 U | 2/2011 |
| CN | 102188241 A | 9/2011 |
| CN | 102711605 A | 10/2012 |
| CN | 102770069 A | 11/2012 |
| CN | 103379855 A | 10/2013 |
| EP | 0 574 027 A2 | 12/1993 |
| EP | 0 648 088 A1 | 4/1995 |
| EP | 0 892 926 B1 | 6/2002 |
| EP | 1 480 557 | 12/2004 |
| EP | 1 850 748 A1 | 11/2007 |
| EP | 2 066 236 A2 | 6/2009 |
| EP | 2 293 056 A2 | 3/2011 |
| GB | 2 472 116 A | 1/2011 |
| JP | S-49-009085 A | 1/1974 |
| JP | S-61-100231 A | 5/1986 |
| JP | H-05-337102 A | 12/1993 |
| JP | 6-58919 A | 3/1994 |
| JP | H-7-116145 A | 5/1995 |
| JP | H-7-284488 A | 10/1995 |
| JP | H-08-299307 A | 11/1996 |
| JP | A-11-160311 A | 6/1999 |
| JP | 2000-037368 A | 2/2000 |
| JP | 2000-506601 A | 5/2000 |
| JP | 2001-502222 A | 2/2001 |
| JP | 2001-516875 A | 10/2001 |
| JP | 2003-000573 A | 1/2003 |
| JP | 2003-505180 A | 2/2003 |
| JP | 2003-527587 A | 9/2003 |
| JP | 2003-529044 A | 9/2003 |
| JP | 2003-529766 A | 10/2003 |
| JP | 2005-519272 A | 6/2005 |
| JP | 2007-083033 A | 4/2007 |
| JP | A-2008-530532 A | 8/2008 |
| JP | 2009-058398 A | 3/2009 |
| JP | 2009-545408 A | 12/2009 |
| JP | 2010-233611 A | 10/2010 |
| JP | 2013-519896 A | 5/2013 |
| JP | 2015-502830 A | 1/2015 |
| JP | 2015-503962 A | 2/2015 |
| WO | WO-97/43952 A1 | 11/1997 |
| WO | WO-98/43539 A1 | 10/1998 |
| WO | WO-97/38307 A1 | 5/2000 |
| WO | WO-00/063683 A1 | 10/2000 |
| WO | WO-03/073935 A2 | 9/2003 |
| WO | WO-03/073935 A3 | 9/2003 |
| WO | WO-2004/032719 A2 | 4/2004 |
| WO | WO-2004/032719 A3 | 4/2004 |
| WO | WO-2005/088289 A1 | 9/2005 |
| WO | WO-2006/086323 A1 | 8/2006 |
| WO | WO-2007/059263 A2 | 5/2007 |
| WO | WO-2007/059263 A3 | 5/2007 |
| WO | WO-2008/019294 A2 | 2/2008 |
| WO | WO-2008/019294 A3 | 2/2008 |
| WO | WO-2008/019680 A2 | 2/2008 |
| WO | WO-2008/019680 A3 | 2/2008 |
| WO | WO-2008/060165 A1 | 5/2008 |
| WO | WO-2008/081449 A2 | 7/2008 |
| WO | WO-2008/081449 A3 | 7/2008 |
| WO | WO-2008/112927 A2 | 9/2008 |
| WO | WO-2008/112927 A3 | 9/2008 |
| WO | WO-2010/097716 A1 | 9/2010 |
| WO | WO-2011/055250 A2 | 5/2011 |
| WO | WO-2011/055250 A3 | 5/2011 |
| WO | WO-2011/070472 A1 | 6/2011 |
| WO | WO-2011/101776 A1 | 8/2011 |
| WO | WO-2012/053910 A1 | 4/2012 |
| WO | WO-2012/059768 A1 | 5/2012 |
| WO | WO-2012/076614 A2 | 6/2012 |
| WO | WO-2012/076614 A3 | 6/2012 |
| WO | WO-2012/146991 A1 | 11/2012 |
| WO | WO-2013/003429 A1 | 1/2013 |
| WO | WO-2013/095284 A1 | 6/2013 |
| WO | WO-2013/096695 A2 | 6/2013 |
| WO | WO-2013/096695 A3 | 6/2013 |
| WO | WO-2014/110181 A1 | 7/2014 |
| WO | WO-2014/127044 A1 | 8/2014 |
| WO | WO-2015/031848 A2 | 3/2015 |
| WO | WO-2015/031848 A3 | 3/2015 |
| WO | WO-2015/031850 A1 | 3/2015 |
| WO | WO-2015/143384 A1 | 9/2015 |
| WO | WO-2016/064925 A1 | 4/2016 |
| WO | WO-2017/130646 A1 | 8/2017 |

OTHER PUBLICATIONS

Coburn, R.F. et al. (1966). "Endogenous Carbon Monoxide Production in Patients with Hemolytic Anemia," Journal of Clinical Investigation 45:460-468.
Ebola Virus Infection (2017). Doctor-clinic.org, 2 total pages.
Extended European Search Report dated Feb. 26, 2016, for European Patent Application No. 12 860 711.6, filed on Dec. 20, 2012, 6 pages.
Extended European Search Report dated Jun. 8, 2016, for European Patent Application No. 14 737 690.9, filed on Jan. 8, 2014, 9 pages.
Extended European Search Report dated Sep. 30, 2016, for European Patent Application No. 14 751 436.8, filed on Feb. 12, 2014, 8 pages.
Extended European Search Report dated Mar. 16, 2017, for European Patent Application No. 14 839 697.1, filed on Aug. 29, 2014, 9 pages.
Extended European Search Report dated Jul. 12, 2017, for European Patent Application No. 14 838 958.8, filed on Aug. 29, 2014, 11 pages.
Extended European Search Report dated Oct. 16, 2017, for European Patent Application No. 15 764 503.7, filed on Mar. 20, 2015, 8 pages.
Final Office Action dated Aug. 24, 2016, for U.S. Appl. No. 13/722,950, filed Dec. 20, 2012, 11 pages.
Final Office Action dated Mar. 21, 2017, for U.S. Appl. No. 14/150,625, filed Jan. 8, 2014, 14 pages.
Final Office Action dated Jun. 7, 2017, for U.S. Appl. No. 14/473,888, filed Aug. 29, 2014, 16 pages.
Final Office Action dated Aug. 16, 2017, for U.S. Appl. No. 14/179,381, filed Feb. 12, 2014, 11 pages.
Final Office Action dated Oct. 19, 2017, for U.S. Appl. No. 14/664,728, filed Mar. 20, 2015, 18 pages.
Final Office Action dated Nov. 20, 2017, for U.S. Appl. No. 14/473,878, filed Aug. 29, 2014, 11 pages.
Final Office Action dated Dec. 29, 2017, for U.S. Appl. No. 13/722,950, filed Dec. 20, 2012, 5 pages.
Final Office Action dated Jun. 5, 2018, for U.S. Appl. No. 14/473,878, filed Aug. 29, 2014, 10 pages.
Final Office Action dated Aug. 24, 2018, for U.S. Appl. No. 14/473,888, filed Aug. 29, 2014, 11 pages.
Final Office Action dated Nov. 9, 2018, for U.S. Appl. No. 14/150,625, filed Jan. 8, 2014, 7 pages.
Final Office Action dated Nov. 1, 2019, for U.S. Appl. No. 14/473,878, filed Aug. 29, 2014, 8 pages.
Final Office Action dated Nov. 1, 2019, for U.S. Appl. No. 14/473,888, filed Aug. 29, 2014, 14 pages.
International Search Report dated May 13, 2013, for PCT Application No. PCT/US2012/071085, filed on Dec. 20, 2012, 4 pages.
International Search Report dated Apr. 15, 2014, for PCT Application No. PCT/US2014/010746, filed on Jan. 8, 2014, 2 pages.
International Search Report dated Apr. 30, 2014, for PCT Application No. PCT/US2014/016105, filed on Feb. 12, 2014, 2 pages.
International Search Report dated Feb. 17, 2015, for PCT Application No. PCT/US2014/053569, filed on Aug. 29, 2014, 5 pages.
International Search Report dated Dec. 18, 2014, for PCT Application No. PCT/US2014/053567, filed on Aug. 29, 2014, 2 pages.
International Search Report dated Dec. 24, 2014, for PCT Application No. PCT/US2014/053572, filed on Aug. 29, 2014, 2 pages.
International Search Report dated Jul. 2, 2015, for PCT Application No. PCT/US2015/021852, filed on Mar. 20, 2015, 2 pages.

(56) References Cited

OTHER PUBLICATIONS

International Search Report dated Feb. 9, 2016, for PCT Application No. PCT/US2015/056527, filed on Oct. 20, 2015, 4 pages.
Jaffe, M.B. (2002). "Mainstream of sidestream capnography?" Medical device depot Inc., White paper, 14 total pages.
Medtronic Capnography brochure MIN 3012492-001/CAT 21300-001569.
Molloy et al., "Are carbon dioxide detectors useful in neonates?" Arch Dis Child Fetal Neonatal Ed (2006) 91:F295-F298.
Non-Final Office Action dated Dec. 1, 2015, for U.S. Appl. No. 13/722,950, filed Dec. 20, 2012, 7 pages.
Non-Final Office Action dated Dec. 18, 2015, for U.S. Appl. No. 14/150,625, filed Jan. 8, 2014, 13 pages.
Non-Final Office Action dated Oct. 21, 2016, for U.S. Appl. No. 14/473,888, filed Aug. 29, 2014, 22 pages.
Non-Final Office Action dated Nov. 10, 2016, for U.S. Appl. No. 14/179,381, filed Feb. 12, 2014, 12 pages.
Non-Final Office Action dated Mar. 13, 2017, for U.S. Appl. No. 13/722,950, filed Dec. 20, 2012, 7 pages.
Non-Final Office Action dated Mar. 23, 2017, for U.S. Appl. No. 14/664,728, filed Mar. 20, 2015, 18 pages.
Non-Final Office Action dated Apr. 20, 2017, for U.S. Appl. No. 14/473,878, filed Aug. 29, 2014, 10 pages.
Non-Final Office Action dated Dec. 15, 2017, for U.S. Appl. No. 14/918,484, filed Oct. 20, 2015, 15 pages.
Non-Final Office Action dated Jan. 8, 2018, for U.S. Appl. No. 14/473,888, filed Aug. 29, 2014, 16 pages.
Non-Final Office Action dated Jan. 9, 2018, for U.S. Appl. No. 14/150,625, filed Jan. 8, 2014, 8 pages.
Non-Final Office Action dated Oct. 18, 2018, for U.S. Appl. No. 14/664,728, filed Mar. 20, 2015, 23 pages.
Non-Final Office Action dated Jan. 10, 2019, for U.S. Appl. No. 14/473,878, filed Aug. 29, 2014, 9 pages.
Non-Final Office Action dated Mar. 12, 2019, for U.S. Appl. No. 14/473,888, filed Aug. 29, 2014, 14 pages.
Non-Final Office Action dated Apr. 29, 2020, for U.S. Appl. No. 14/473,878, filed Aug. 29, 2014, 9 pages.
Non-Final Office Action dated May 18, 2020, for U.S. Appl. No. 14/473,888, filed Aug. 29, 2014, 14 pages.
Notice of Allowance dated Mar. 30, 2018, for U.S. Appl. No. 13/722,950, filed Dec. 20, 2012, 7 pages.
Notice of Allowance dated Aug. 12, 2019, for U.S. Appl. No. 14/150,625, filed Jan. 8, 2014, 8 pages.
Partial Supplementary European Search Report dated Apr. 7, 2017, for European Patent Application No. 14 838 958.8, filed on Aug. 29, 2014, 7 pages.
RESTEK Product catalog 2011/2012 https://www.calameo.com/books/00004252746f79e5d8c85 (Year: 2012), 1 total page.
Written Opinion of the International Searching Authority dated May 13, 2013, for PCT Application No. PCT/US2012/071085, filed on Dec. 20, 2012, 6 pages.
Written Opinion of the International Searching Authority dated Apr. 15, 2014, for PCT Application No. PCT/US2014/010746, filed on Jan. 8, 2014, 6 pages.
Written Opinion of the International Searching Authority dated Apr. 30, 2014, for PCT Application No. PCT/US2014/016105, filed on Feb. 12, 2014, 5 pages.
Written Opinion of the International Searching Authority dated Feb. 17, 2015, for PCT Application No. PCT/US2014/053569, filed on Aug. 29, 2014, 6 pages.
Written Opinion of the International Searching Authority dated Dec. 18, 2014, for PCT Application No. PCT/US2014/053567, filed on Aug. 29, 2014, 5 pages.
Written Opinion of the International Searching Authority dated Dec. 24, 2014, for PCT Application No. PCT/US2014/053572, filed on Aug. 29, 2014, 5 pages.
Written Opinion of the International Searching Authority dated Jul. 2, 2015, for PCT Application No. PCT/US2015/021852, filed on Mar. 20, 2015, 8 pages.
Written Opinion of the International Searching Authority dated Feb. 9, 2016, for PCT Application No. PCT/US2015/056527, filed on Oct. 20, 2015, 6 pages.
Final Office Action dated Jan. 15, 2021, for U.S. Appl. No. 14/473,888, filed Aug. 29, 2014, 16 pages.
Final Office Action dated Feb. 2, 2021, for U.S. Appl. No. 14/473,878, filed Aug. 29, 2014, 12 pages.
Non-Final Office Action dated Sep. 3, 2020, for U.S. Appl. No. 16/044,902, filed Jul. 25, 2018, 9 pages.
Non-Final Office Action dated Jan. 6, 2021, for U.S. Appl. No. 16/008,594, filed Jun. 14, 2018, 14 pages.
Non-Final Office Action dated Mar. 24, 2021, for U.S. Appl. No. 16/386,034, filed Apr. 16, 2019, 25 pages.
Sanchez, A. (2004). "Analysis of Human Peripheral Blood Samples from Fatal and Nonfatal Cases of Ebola (Sudan) Hemorrhagic Fever: Cellular Responses, Virus Load, and Nitric Oxide Levels," J. Viral. 78:10370-10377.
Final Office Action dated Sep. 30, 2021, for U.S. Appl. No. 16/008,594, filed Jun. 14, 2018, 18 pages.
Final Office Action dated Nov. 10, 2021, for U.S. Appl. No. 16/386,034, filed Apr. 16, 2019, 23 pages.
Non-Final Office Action dated Sep. 16, 2021, for U.S. Appl. No. 16/678,759, filed Nov. 8, 2019, 13 pages.
Non-Final Office Action dated Aug. 9, 2021, for U.S. Appl. No. 14/473,878, filed Aug. 29, 2014, 9 pages.
Notice of Allowance dated Mar. 15, 2021, for U.S. Appl. No. 16/044,902, filed Jul. 25, 2018, 7 pages.
Notice of Allowance dated Aug. 2, 2021, for U.S. Appl. No. 14/473,888, filed Aug. 29, 2014, 8 pages.

* cited by examiner

— 314: Pneumatic flow pathway
----- 316: Pneumatic connection
— — — 318: electrical connection ——————— 314: Pneumatic flow pathway
················ 316: Pneumatic connection
— — — — 318: electrical connection

SAMPLING AND STORAGE REGISTRY DEVICE FOR BREATH GAS ANALYSIS

CROSS-REFERENCE TO RELATED APPLICATIONS

This application is a continuation of U.S. application No. 14/179,381 filed on Feb.12, 2014, which claims the benefit of U.S. Provisional Application Nos. 61/763,896 and 61/794,254filed on Feb. 12, 2013 and Mar. 15, 2013, respectively, the disclosures of which are hereby incorporated by reference in their entireties.

FIELD

Described herein are devices and methods for the analysis of breath exhalant for diagnostic purposes. More specifically, devices and methods are described for sampling and analyzing a relevant portion of the breathing cycle, for example end-tidal gas, from a person's breath. The devices and method may be used, for example, to correlate the gas analysis to an underlying physiologic condition for diagnostic, monitoring or screening purposes, or in conjunction with a therapeutic treatment.

BACKGROUND

Certain metabolites and chemicals produced in or entering the body and blood stream are excreted in the breath. The level in the body or blood stream may be determined by measuring it in the breath. For example, breath carbon monoxide (CO) levels may be measured to detect and monitor underlying disorders such as hematological disorders and conditions, metabolic disorders, and environmental and behavioral problems. For example, end-tidal CO can be correlated to blood CO, which can be indicative of hemolysis, smoking or inhalation poisoning. In order to measure end-tidal CO, alveolar gas may be collected non-invasively from the exhaled breath of a patient, by capturing the portion of the breath at the end of exhalation. The captured end-tidal gas can then be analyzed for its CO concentration thus completing the non-invasive measurement. Typically, a correlation exists between the end-tidal gas level and the level of the metabolite or chemical in the body or blood, for example a 1:1 ratio or some other ratio.

Typically, but not always, two types of sensors are used; a breath monitoring sensor and a gas analysis sensor. For breath monitoring, in order to precisely target and collect the appropriate section of the breathing pattern, typically a real-time or nearly instantaneous sensing technology is used to measuring the breathing pattern, such as an infrared $CO_2$ sensor. Or other sensors such as airway pressure sensors, flow sensors, oxygen gas sensors, chest impedance sensors, acoustic sensors, vibration sensors, and diaphragmatic movement and innervation sensors. For gas composition analysis, in order to meet the requisite clinical accuracy, the available sensors that meet this purpose typically require a substantial signal response time that is significantly longer than the duration of a single breath. Therefore, in accurate systems, the gas analysis step may take place after the breathing pattern monitoring and gas sample collection step.

There may be some significant limitations with conventional breath analysis systems. Specifically, in a first limitation it has been reported that due to irregular breathing patterns, obtaining and analyzing a proper end-tidal gas sample is often problematic and in some cases not possible. Determining whether or not a particular breath is a "normal" breath consisting of a valid alveolar gas composition in its exhalation phase, often cannot be determined until after a series of breaths or a substantial duration of breathing is analyzed. "Capnography", by J. S. Gravenstein, Michael B. Jaffe, Nikolaus Gravenstein describes numerous paradigms where breath analysis would be useful but cannot be completed due to underlying irregularities. Most of the analyses shown in the book assume "artifact free" waveforms, and the authors acknowledge that this is rarely the case, especially in diseased patients, intubated patients, and other commonly occurring clinical events. In addition, clinical trials related to breath analysis typically have to exclude patients with irregular, erratic or unpredictable breathing patterns. Medtronic Capnography brochure MIN 3012492-001/CAT 21300-001569 displays a series of capnographic waveforms all of which routinely occur in clinical settings as a result of disease, airway obstruction, apnea, inadequate breath, etc. Many of these conditions would make detailed measurements of chemical composition of breath difficult, inaccurate, or impossible. Further, as is obvious to anyone skilled in the art, analysis of gases such as CO, $H_2$ and nitric oxide may be an order of magnitude more complex than the measurement of $CO_2$ concentration, the subject of most of the references cited above. This means that when $CO_2$ concentration cannot be reliably obtained, than most probably no other gas concentration measurements can be obtained either.

In a second limitation, it has been realized that conventional breath gas analysis devices may either miss important information by: (a) measuring only one individual breath, thereby missing potentially very useful information contained in a different breath; or by (b) volumetrically combining all the breaths within a series of breaths in a chamber, thereby diluting the information contained in an important breath. The systems may also be limited in that if measuring all the breaths within a series of breaths, valid and invalid breaths are combined thus potentially diluting the accuracy of the result.

Several issued U.S. patents and published patent applications discuss state of the art in breath analysis. U.S. Pat. No. 6,544,190 B1 discloses that the system described "provides a means to reject test data when excessive breath variability likely makes the test unreliable." Medtronic application Ser. No. 11/588,990, publication number US 2008/0009762 A1 describes an algorithm to analyze capnographic data by providing a non-linear fit to the shape of the capnography curve, but does not address any underlying chemical analysis of the breath. Similarly, U.S. Pat. No. 6,428,483 (issued to Oridion) describes a capnographic waveform analysis system which considers angles of the waveform, transition points, and other characteristics, but it operates on one breath at a time, in real time, and has no storage mechanism. Next, U.S. Pat. No. 6,733,463 describes a nitric oxide measurement system which tries to control the exhalation flow rate, but this also is not applicable to breaths with variable flow and rate characteristics. U.S. Pat. No. 8,021,308 describes a method of isolating the end tidal portion of the breath, by finding the transition point between exhalation and inhalation, and then analyzing that portion of the breath, in real time. While that invention has adjustable analysis methodology based on the breath rate, it is limited to identifying a transition point or portion of the current breath (such as end tidal), and it does not provide a means for subsampling the stored volume, or subsequent adaptation of beginning and ending sampling points. Further, it doesn't provide means for storing multiple full breaths. U.S. Pat. No. 6,582,376 describes a measurement system for alveolar breath analysis, and provides a sample volume to store a portion of the breath based on a threshold, but it does not allow for separate identification of individual breaths.

SUMMARY

Described herein are methods, systems and devices that analyze gases, particles and other substances in the breath by organizing a physical registry of a series of breaths and/or sections from individual and/or multiple breaths, characterizing the breath types and breath section types within that registry, organizing the different segments within that registry, and conducting the desired analysis on the desired breaths and/or desired breath sections, in real time, or after a period of time has elapsed.

To address the problems associated with conventional state-of-the-art approaches, a more powerful and useful gas analysis technology in some variations employs a breath storage and breath information registry. For example in some variations, the breath analyzer may analyze in detail a series of breaths, and collect multiple samples and sub-samples from that series, then after the breathing pattern and breath types of the series are analyzed and the information organized in a registry, the system may either combine the samples together for further analysis, or combine and/or segregate them in different ways for further analysis, or separate them for individual different types of analyzes, all based on a characterization and comparison of the breath types in the series of breaths.

In a first variation, gas from a breath or series of breaths are drawn from a patient and the breath types and breath section types of each section of gas are defined analyzing using a breathing signal from a breathing sensor, preferably but not always a fast, instantaneous or near-instantaneous breathing sensor, and the requisite algorithms. The breathing signal contains indications of timing markers in a breath cycle, and may, for example, be obtained using IR sensors tuned to a breathing gas type, or multiple gas types, such as in capnography. The breath gas itself may be captured into a sample collection compartment with a small cross-sectional flow path to reduce mixing between constituent sections of gas from different sections of a breath, and between breaths. The different constituent sections may be cataloged in a registry, based on the breathing signal. Desired sections may be analyzed to determine the level of a gas of interest.

In a second variation, the breath gas is captured into different sample collection compartments each with a small cross-sectional flow path to reduce mixing between constituent sections of gas. The different constituent sections of the different compartments may be cataloged in a registry, using the breathing signal. Desired sections may be analyzed by different sensor types to determine the level of different gases of interest.

In a third variation, breath gas is captured into a sample collection compartment with a small cross-sectional flow path to reduce mixing between constituent sections of gas. The different constituent sections may be cataloged in a registry. Desired sections may be analyzed by various different sensors to determine the level of various gases in question.

In a fourth variation, breath gas is captured into different sample collection compartments each with a small cross-sectional flow path to reduce mixing between constituent sections of gas. The different constituent sections of the different compartments may be cataloged in a registry. Desired sections may be analyzed to determine the level of a substrate in question.

In additional variations, an appropriate gas such as ambient gas or an inert gas is inserted in between different constituent sections of gas in the sample compartment to help separate the sections. In other variations, a particular portion of a breath such as the end-tidal portion, is collected and collated from multiple breaths and analyzed. In other variations, different pneumatic configurations of flow pumps, sample collection compartments and substrate analysis sensors are described.

In some variations, a breath gas capture device does not include an analysis sensor, and the sample compartment is transported to a sensor after the gas is captured. For example, the gas may be captured at the patient bedside, doctor's office or remotely at home or in the field, then transported to a laboratory for analysis. In other variations, different sections of the breath may be organized in the registry for appropriate analysis. For example, upper airway analytes may contain the sample of interest, or middle airway analytes, or lower airway analytes, or alveolar analytes, or a combination thereof, depending on the diagnostic test(s) desired. The system can be fully programmable by the user, such that the user can enter the type of analysis to be undertaken, and the system then executes the necessary control systems and algorithms to collect, organize and analyze the necessary samples. In other variations, the test subject may be commanded by the user or the system to perform certain breathing maneuvers while the breath samples are being collected. For example, the user can submit a breath hold, or a deep breath, or a shallow breath, or a normal tidal volume breath, or combinations thereof. This may increase the resolution of the system in cases in which an analyte indicative of the disease in question is most noticeable in a certain breath type. The system may validate and accept or reject each sample based on measuring the actual submitted breath and comparing against expected breathing pattern signals. Or, the test subject may be subjected to a challenge maneuver for example in which he or she is instructed to breathe or inject a tracer element or provoking agent, and in which the resulting analytes in the breath change as a result, indicative of the underlying pathology or disease or syndrome under question. It should be understood that the systems described in this disclosure may include obtaining samples from a non-cooperative subject as well as cooperative subjects.

In a fifth variation, a breath sampling and analysis apparatus includes: a sensor that detects a gas parameter for determining the start point and end point of different breath portions; a pump that draws at least one gas sample from a person's breath; and a sample compartment that stores breath portions each in separate physical locations.

In a sixth variation, the breath analysis apparatus of the fifth variation further includes an analyzer that analyzes separately each of the stored breath portions for a parameter.

In a seventh variation, the sample compartment of the fifth variation comprises a capillary channel in which the different breath portions occupy sections of volume of the channel, and wherein the sections are end to end.

In an eighth variation, the separate physical locations of the fifth variation comprises separate sample containers, and wherein the apparatus further comprises a manifold system to divert the different breath portions into the separate sample containers.

In a ninth variation, the each sample container of the eighth variation comprises a respective bypass tube and a respective sensor.

In a tenth variation, the each sample container of the eighth variation comprises a respective sensor, and wherein the apparatus comprises one bypass tube for all sample containers.

In an eleventh variation, the breath analysis apparatus of the eighth variation comprises one sensor for all sample containers and one bypass tube for all sample containers.

In a twelfth variation, the breath portions of the fifth variation are from a single breath.

In a thirteenth variation, the breath portions of the fifth variation are from different breaths.

In a fourteenth variation, the breath analysis apparatus of the fifth variation includes an analyzer that analyzes one or more breath portions for a first parameter.

In a fifteenth variation, the analyzer of the fourteenth variation analyzes another one or more breath portions for a second parameter.

In a sixteenth variation, the breath analysis apparatus of the fifth variation includes an analyzer that analyzes the breath portions together.

In a seventeenth variation, the breath analysis apparatus of the fifth variation includes an analyzer that analyzes the breath portions separately.

In an eighteenth variation, the breath analysis apparatus of the fifth variation includes a processor to identify a desired breath portion by receiving measurements of a breathing pattern characteristic, and wherein the sample compartment receives gas from the desired portion of the breath.

In a nineteenth variation, a breath sampling and analysis apparatus includes: a sensor that identifies the beginning and end of a breath, thereby dividing the breath pattern into different breath portions identifying the beginning and end of different breath portions; a vacuum pump that draws a gas sample from a person's breath into at least one sample tube, the sample tube comprising gas from at least one breath and at least one breath portion; and a computer to identify the location of gas in the sample tube corresponding to the beginning and end of the breath, and corresponding to the beginning and end of the breath portion.

In a twentieth variation, the breath analysis apparatus of the nineteenth variation includes an analyzer that analyzes the stored breath samples for a parameter.

In a twenty-first variation, a breath sampling apparatus includes: a sampling tube configured to prevent mixing within the tube of breath exhaled by a patient; an inlet valve and an outlet valve coupled to the sampling tube, wherein the inlet valve and outlet valve together are operable to capture the breath exhaled by the patient within the sampling tube; and an inlet tube fluidly coupled to the sampling tube, wherein the inlet tube is operable to directly receive the breath exhaled by the patient, and wherein the inlet valve is further operable to isolate the sampling tube from the inlet tube.

In a twenty-second variation, the breath sampling apparatus of the twenty-first variation includes a processor for determining a position in the storage tube of a segment of the exhaled breath.

In a twenty-third variation, the breath sampling apparatus of the twenty-first variation includes an in-flow sensor for determining one or parameters of the exhaled breath in the sampling tube.

In a twenty-fourth variation, the in-flow sensor of the twenty-third variation includes one or more selected from the group consisting of a flow rate sensor, a MEMS fluidic sensor, an optical bench, and a mass spectrometer.

In a twenty-fifth variation, the processor of the twenty-third variation determines the position of the segment by referencing a record of parameters of the exhaled breath in the sampling tube, wherein the record is populated by the one or more parameters determined by the in-flow sensor.

In a twenty-sixth variation, the one or more parameters of the twenty-fifth variation includes one or more selected from the group consisting of a time profile of the exhaled breath entering the sampling tube, a flow rate profile of the exhaled breath, a pump-speed profile of a pump coupled to the sampling tube, a pressure profile of the exhaled breath, a carbon dioxide concentration profile of the exhaled breath, and a temperature profile of the exhaled breath.

In a twenty-seventh variation, the breath sampling apparatus of the twenty-first variation includes an analyzing system for determining a characteristic of a segment of the exhaled breath after it is captured in the sampling tube.

In a twenty-eighth variation, the analyzing system of the twenty-seventh variation includes one or more storage containers, wherein the one or more storage containers are fluidly coupled to the sampling tube, and wherein the outlet valve is operable to isolate the sampling tube from the one or more storage containers.

In a twenty-ninth variation, the analyzing system of the twenty-seventh variation an exhaust for venting segments of the exhaled breath.

In a thirtieth variation, the analyzing system of the twenty-seventh variation analyzes a characteristic of one or more gases selected from the group consisting of anesthesia gases, poisonous gases, metabolic gases resulting from alcohol use, metabolic gases resulting from drug use, metabolic gases resulting from disease, and hydrogen.

In a thirty-first variation, the breath sampling apparatus of the twenty-first variation includes a pump fluidly coupled to the sampling tube, wherein the outlet valve is operable to isolate the sampling tube from the pump.

In a thirty-second variation, the pump of the thirty-first variation has a variable speed.

In a thirty-third variation, the pump of the thirty-first variation has a reversible flow direction.

In a thirty-fourth variation, the sampling tube of the twenty-first variation has a capillary tube.

In a thirty-fifth variation, the sampling tube of the twenty-first variation is configured to store a plurality of exhaled breaths.

In a thirty-sixth variation, the plurality of exhaled breaths of the thirty-fifth variation are exhaled by a plurality of patients.

In a thirty-seventh variation, a method of analyzing one or more breaths includes: storing the one or more breaths in a sampling tube configured to prevent mixing of the breath within the sampling tube; recording one or more characteristics of the breath stored in the sampling tube; identifying one or more segments of the breath stored in the sampling tube, wherein the identification of the one or more segments is based upon the recorded characteristics of the breath; extracting the one or more segments from the sampling tube; and analyzing the one or more segments.

In a thirty-eighth variation, the recording the one or more characteristics of the breath of thirty-seventh variation includes determining the one or more characteristic with an in-flow sensor.

In a thirty-ninth variation, the in-flow sensor of the thirty-eighth is configured to determine one or more selected from the group consisting of a time profile of the exhaled breath entering the sampling tube, a flow rate profile of the exhaled breath, a pump-speed profile of a pump coupled to the sampling tube, a pressure profile of the exhaled breath, a carbon dioxide concentration profile of the exhaled breath, and a temperature profile of the exhaled breath.

In a fortieth variation, the extracting the one or more segments of the breath in the thirty-seventh variation includes exhausting unwanted segments.

In a forty-first variation, the extracting the one or more segments of the breath in the thirty-seventh variation includes storing the one or more segments in one or more storage containers.

In a forty-second variation, the extracting the one or more segments of the breath in the thirty-seventh variation includes returning unwanted segments to the sampling tube using a pump with a reversible flow.

In a forty-third variation, the analyzing the one or more segments of the breath in the thirty-seventh variation includes analyzing a characteristic of one or more gases selected from the group consisting of anesthesia gases, poisonous gases, metabolic gases resulting from alcohol use, metabolic gases resulting from drug use, metabolic gases resulting from disease, and hydrogen.

In a forty-fourth variation, the analyzing the one or more segments of the breath in the thirty-seventh variation includes analyzing at least one selected from the group consisting of breath segments from a plurality of breaths, an end-tidal concentration of one or more breaths, and an alveolar concentration of one or more breaths.

In a forty-fifth variation, the storing the one or more breaths in the thirty-seventh variation includes storing the one or more breaths in a capillary tube.

In a forty-sixth variation, the storing the one or more breaths in the thirty-seventh variation includes storing a plurality of breaths from a plurality of patients.

In a forty-seventh variation, the storing the one or more breaths in the thirty-seventh variation includes drawing the breath into the sampling tube with a pump.

In a forty-eighth variation, the pump of the forty seventh-variation has a variable flow rate.

In a forty-ninth variation, a breath sampling apparatus includes: a sampling tube configured to prevent mixing of exhaled gases within the sampling tube; and first and second valves coupled to the sampling tube, wherein the first and second valves are configured to capture exhaled breath within the sampling tube.

In a fiftieth variation, a method of analyzing one or more breaths includes: identifying one or more constituent portions of the one or more breaths; storing the one or more breaths so the one or more constituent portions are not mixed; identifying at least one of the one or more constituent portions for analysis; and analyzing the at least one of the one or more constituent portions.

In a fifty-first variation, a method of analyzing a breaths includes: storing the breath so that one or more constituent portions of the breath are not mixed; and analyzing at least one of the one or more constituent portions.

Variations disclosed herein may have the following benefits. First, a breath, or multiple breaths, can be physically stored, while preserving accurate timing and breath type information for each breath, and each section of each breath. This allows for any portion of the breath(s) to be independently analyzed for the chemical composition under interest. It also allows for a breath or section of breath to be chosen for analysis after comparing and contrasting its breath type against thresholds and against other breath types in a series of breaths. It also allows for different breath types to be sought and chosen for different types of compositional analyses. Second, variations herein prevent undesired mixing of the breath sample, for example the end-tidal sample, with the ambient or other portions of the breath, or other breaths, by selecting a proper size of the storage apparatus and appropriate isolation valves, pneumatic routing of the gas, and precise valve control. Third, variations herein include adding an inert gas as necessary to maintain relative concentration of gasses of interest. This may be useful when the overall volume of the collected breath is too small to be effectively moved around the apparatus of measured, and also to avoid the mixing in of the ambient air into the stored samples. Fourth, variations herein include varying the gas sampling flow rate to collect incoming breath gas at variable speed, covered in more detail in U.S. patent application Ser. No. 13/722,950, assigned to the assignee of the present application, the disclosure of which is incorporated by reference herein in its entirety.

Separately, the derivation of the breathing signal can be accomplished using various algorithms for analysis of a breath waveform to determine a breath segmentation to achieve a specific objective: increased volume of specific breath portions, increased accuracy by sampling smaller sections of the breath, end tidal concentration, alveolar concentration, etc. These algorithms may affect the decision making for time markers for one breath which are dependent on the shape and number of one or more additional breaths. This may particularly be the case when a specific breathing pattern is identified, say for a known pathology, for which several breaths needs to be collected. Algorithms for identifying time markers for each of the breaths collected during the sampling period may subsequently be adjusted as new breaths come in. The time markers identified from the breathing signal may then be used to correctly identify breath portions to group together, to obtain sufficient volume to be measurable by the sensors.

DETAILED DESCRIPTION

Described here are devices and methods for creating a breath gas sample registry, and analyzing the gas in that registry for a desired monitoring, screening or diagnostic purpose. In the embodiments shown, for exemplary purposes, the patient's breath sample is shown to be drawn into the instrument from the patient by application of vacuum. However the disclosure also applies to patients breathing into the instrument in order for the instrument to collect the breath sample, without the vacuum application.

In some variations, one or more breathing parameters are measured to identify the different constituent portions of a breath and the respective time periods, and a pneumatic system is used for capturing the portion of exhaled breath in a sampling tube using the identified time period. In some variations, one or more valves and/or flow control mechanisms—such as a vacuum pump, for example—are used to regulate the flow rate of gas drawn into the sampling tube. In some variations, the captured portion of breath is analyzed for indications of a patient's physiological state.

Measured breathing parameters may include one or more of carbon dioxide, oxygen, airway pressure, airway temperature, breath flow rate, chest impedance, diaphragmatic movement or innervation, breath sounds, or breath vibrations. Identifying the time period of a portion of a breath may include identifying substantially the start, midpoint and termination of that time period.

A diagnostic gas sample may be best taken from the end-tidal period, for example when attempting to diagnose a physiologic condition in the blood stream, such as hemolysis. For explanatory purposes, exemplary variations for sampling end-tidal gas for end-tidal CO measurement are given below; however the principles apply to other diagnostic purposes.

Figure 1:
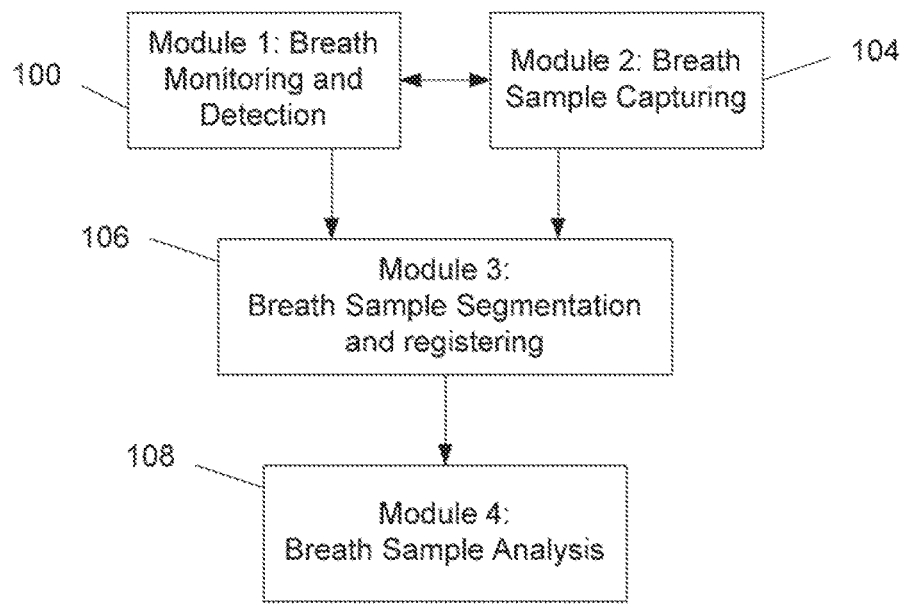
FIG. 1 describes a flow chart of a basic sequence of operation of an analyzer in which segmentation of the breath samples occurs in series with monitoring and capturing of the samples, in accordance with one variation.

FIG. 1 describes the basic sequence of operation of the device, in accordance with one variation. The first module or algorithm 100 performs the breath monitoring and detection function. In this module, the breathing pattern of a person is monitored, typically with an instantaneous or near-instantaneous sensor. The breathing pattern information provides all the relevant and useful information about the breaths and sections of breaths over a series of breaths. The information is used for categorizing and typifying breaths and sections of breaths, and is time based to define the timing associated with the different breaths and sections of breaths. The second module or algorithm 104 performs the breath sample capturing function, which can take place in parallel with the breath monitoring and detection module. In this module, the collected gas is segmented into its constituent parts, and the constituent parts are physically separated, or identified with a time or location identification. The third module or algorithm 106 performs breath type characterization, based on information from the breath monitoring and detection module, and catalogs each breath and each section of each breath into a registry along with relevant information regarding each breath and section. The characterization may be made using criteria that may be predefined, or defined in real-time, or user-defined, automatically defined or semi-automatically defined. For example, predefined criteria may be absolute or relative threshold parameters stored in the device's software. Or a user may enter certain information relative to the specific test being performed, and the system may use that information to define the criteria. Or the system can automatically establish the criteria in real time based on the prevailing conditions, or for a known or identified patient pathology, where certain breath patterns may be more likely to occur. Or a combination of the above techniques can be employed. In this module, the software algorithms decide which breath or breaths, or which section of breath or breaths, will be analyzed and for what analysis. Finally in a fourth module or algorithm 108, the sample or samples are transferred from its storage location to the associated sensor for compositional analysis or analyses.

Figure 2:
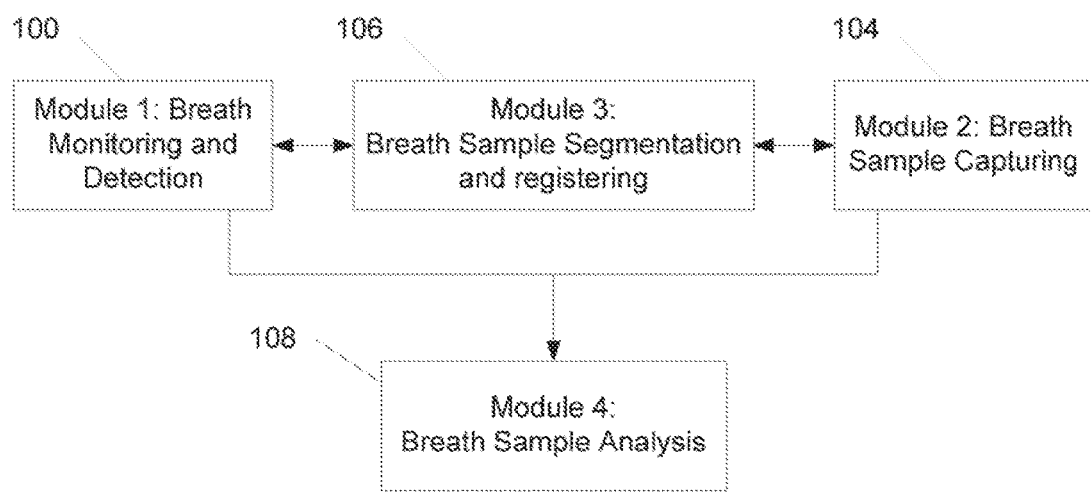
FIG. 2 describes a flow chart of a basic sequence of operation of an analyzer in which segmentation of the breath samples occurs in parallel with monitoring and capturing of the samples, in accordance with one variation.

FIG. 2 schematically describes an alternate sequence of operation of the device in which modules 100, 104 and 106 may occur in parallel, or substantially in parallel, or partially in parallel, in accordance with one variation.

Figure 3:
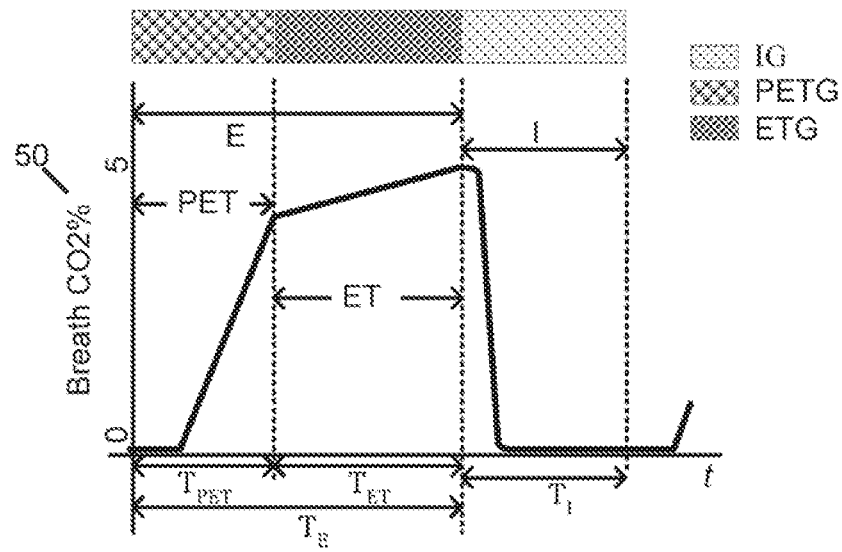
FIG. 3 graphically describes a typical breath monitoring waveform based on a carbon dioxide measurement which is taken on the gas being drawn from the breath, in accordance with one variation.

FIG. 3 graphically describes a typical breathing pattern from the perspective of a carbon dioxide ($CO_2$) signal measured in breath drawn from the person's airway, such as from their nose, as a function of time, with time t on the horizontal axis, and $CO_2$ level 50 on the vertical axis, in accordance with one variation. During the expiratory phase E $CO_2$ is expelled, hence the $CO_2$ level increases. During the inspiratory phase I ambient air occupies the nose, hence the measured $CO_2$ drops to essentially zero. There may be a variety of shapes to a breath $CO_2$ curve, based on the person's breathing pattern, their age, how they are breathing and any underlying acute or chronic medical conditions. A classic curve may show the following sub-portions for the expiratory phase: (1) a beginning portion of pre-end-tidal gas PETG, containing low or no $CO_2$ because the gas may simply be gas from the proximal airway devoid of $CO_2$, (2) a middle portion of pre-end-tidal gas PETG, containing $CO_2$ rapidly increasing from zero to the $CO_2$ level at the distal segments of the lungs, and (3) an end-portion of end-tidal gas ETG showing a plateauing or leveling off of the $CO_2$, representing the $CO_2$ coming from the alveoli for that exhaled breath, and (4) potentially a constant peak level at the very end of the expiratory period, and (5) an inspiratory section of inspiratory gas (IG). However, there can be many other curves different from this classic curve. Peak $CO_2$ levels are typically 4-6% during the end-tidal period and close to or equal to zero during the inspiratory period.

In some variations, the level of $CO_2$ in an exhaled breath is used to determine the duration of a period of a breath. In further variations, duration of a period of breath may be characterized by a start and a termination of that period. In some variations, a $CO_2$ level is used to determine a start or a termination of a period of a breath. Some examples include inspiratory time Ti, expiratory time Te, pre-end-tidal time Tpet, end-tidal time Tet, post expiratory time Tpe. In other variations, a first time derivative of a $CO_2$ level is used to determine a start or a termination of a period of a breath. In yet other variations, a second time derivative of a $CO_2$ level is used to determine a start or a termination of a period of a breath. In some variations, a combination of $CO_2$ levels and $CO_2$ level time derivatives may be used to determine a start or a termination of a period of a breath. In some variations, a start of an end-tidal period may be determined by a change in the first time derivative of a $CO_2$ level of the exhaled breath, such as a sudden decrease in the first time derivative of the $CO_2$ level. In some variations, a decrease in the first time derivate of the $CO_2$ level is more than a 10% decrease. In some variations, a decrease in the first time derivate of the $CO_2$ level is more than a 25% decrease. In some variations, the derivative will approach or become zero showing very little rate of change or a peak plateau respectively. In other variations, the start of an end-tidal period may be determined by a large second time derivative of the $CO_2$ level. In some variations, a termination of an end-tidal period may be determined by a maximum $CO_2$ level, which may be detected or confirmed by a change in the sign of the first time derivative of the $CO_2$ level as the derivative becomes negative associated with a drop of the $CO_2$ level from its peak value. In further variations, a start of a beginning period may be determined by a sudden increase in the first time derivative of the $CO_2$ level. In other variations, the start of a beginning period may be determined by an increase in the $CO_2$ level from zero $CO_2$ level. In some variations, a termination of a middle period may be determined by a change in the first time derivative of a $CO_2$ level of the exhaled breath, such as a sudden decrease in the first time derivative of the $CO_2$ level. In some variations, a $CO_2$ level, first time derivative thereof, or second time derivative thereof may be used to determine the start and termination of one or more periods. In another variation, a pattern matching algorithm may be employed to analyze the shape of the $CO_2$ waveform. Other breath-borne gases may be used in place of $CO_2$ for measuring the breathing curve. For example, oxygen can be measured which would indicate a higher oxygen concentration during inspiration than expiration. It is also contemplated that the breathing pattern may be instantaneously or substantially instantaneously measured by a fast-responding CO sensor. In this case referring to FIG. 1, the sensor 10 may be a fast responding CO sensor that depicts the breathing pattern and also measures the end-tidal CO level. After application of the various breath qualification and disqualification variations described subsequently, the CO level of a qualified breath can be reported as the result.

Figure 4:
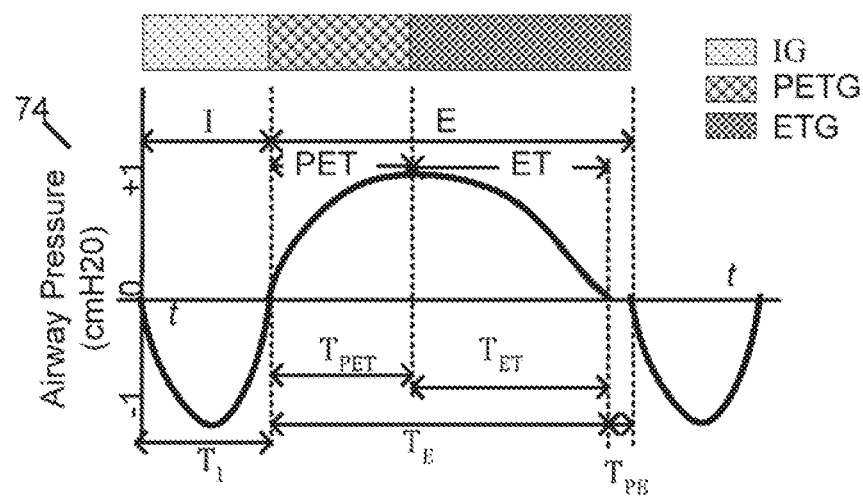
FIG. 4 graphically describes a typical breath monitoring waveform based on an airway pressure measurement taken at the proximal airway, in accordance with one variation.

FIG. 4 graphically describes a typical breathing signal from the perspective of measured airway pressure with airway pressure 74 on the vertical axis and time t on the horizontal axis, in accordance with one variation. The airway pressure shows a negative pressure during inspiratory phase and a positive pressure during expiratory phase. Typically during at rest breathing the peak expiratory pressure may correspond to the middle of the expiratory phase and the start of the end-tidal period. In FIGS. 3 and 4, TI, TE, TPET, TET, TPE represent inspiratory time, expiratory time, pre-end-tidal time, end-tidal time, and post expiratory time respectively. An inspiratory pause may also be present (not shown), in which the peak of lung muscle movement during inspiration is paused before the expiratory period begins. Peak inspiratory pressure may be −1 to −4 cwp during restful breathing, and up to −15 cwp during heavier breathing, and peak expiratory pressure may be +0.5 to +2.0 cwp during restful breathing and up to +10 cwp during heavier breathing when measured at the entrance to the nostrils. Airway pressure can be measured with a secondary lumen in the sampling cannula, extending the length of the cannula, or can be measured by teeing into the sampling cannula or by placing a sensing transducer at the airway of the patient.

In some variations, airway pressure is used to determine a start or a termination of a period of a breath. In other variations, a first time derivative of an airway pressure is used to determine a start or a termination of a period of a breath. In yet other variations, a second time derivative of an airway pressure is used to determine a start or a termination of a period of a breath. In some variations, a combination of airway pressures and airway pressure time derivatives may be used to determine a start or a termination of a period of a breath. In some variations, a start of an end-tidal period is determined by maximum airway pressure, that is, by a zero first time derivative of the airway pressure. In some variations, a termination of an end-tidal period may be determined by zero airway pressure. In some variations, an airway pressure, first time derivative thereof, or second time derivative thereof may be used to determine the start and termination of one or more periods. In some variations, a pattern matching algorithm can be utilized to identify relevant time markers of the breaths.

In some variations, the breath sensor monitors the person's breathing over time, and trends the breathing pattern by determining a continually updated value that is characteristic of the breathing pattern. For example, peak positive values of a breathing signal may be measured and updated for each breath. Peak values may be compared with previous peak values. Peak values may be averaged over a previous number of multiple breaths. Similarly, time-related aspects of the breaths may be trended, such as the expiratory time. Various breath-related events that are not normal breaths may be identified and exception algorithms may exist in order to not include these non-normal breath events inadvertently in deterministic steps. For example, the characteristic waveform of a sneeze, cough, stacked breath, or non-full breath may be defined in advanced or based on monitoring of a particular patient, and when detected by the breathing sensor, excepted from the appropriate deterministic algorithms.

Figure 5:
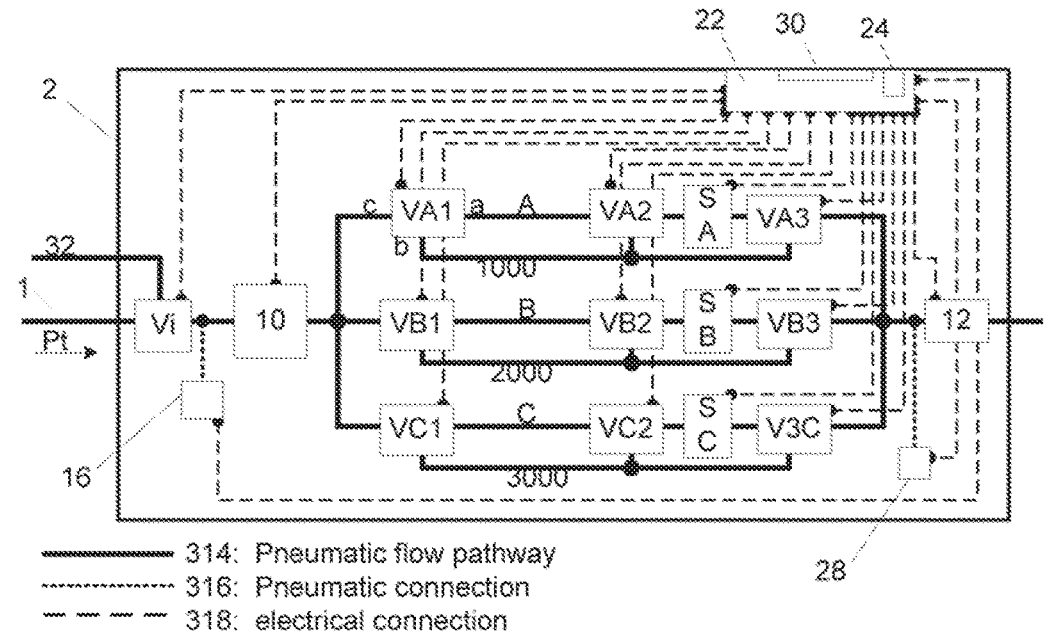
FIG. 5 is a schematic diagram of an exemplary analyzer capable of organizing a registry of separate gas samples, for example for analyzing more than one breath and for more than one substance, in accordance with one variation.
Figure 6:
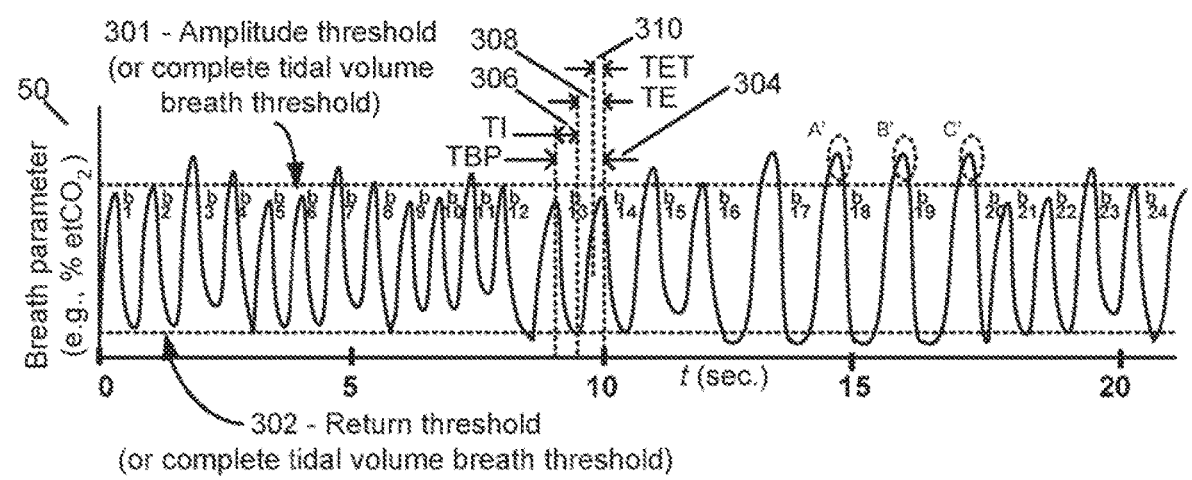
FIG. 6 describes a capnometry plot of a series of breaths that are considered for analysis by the instrument shown in FIG. 5, with three certain breath types sought, identified, captured and analyzed, in accordance with one variation.

FIG. 5 describes schematically one variation of a device for capturing exhaled breath, with multiple sample collection tubes and multiple sample composition analyzers. Pneumatic flow paths 314, pneumatic connections 316 and electrical connections 318 are shown. The system includes a sampling cannula 1 and a sample collection and analysis instrument 2. Gas may be drawn from the patient Pt, for example using a sampling cannula 1 and a flow generator 12. The flow rate of the flow generator may be measured by a flow transducer, for example a pressure sensor array, 16 and 28, arranged like a pneumotach. The measured flow rate may be used as a closed loop feedback control to control the flow generator flow rate. A breath sensor, such as a capnometer 10 or a pressure sensor 16, is used to measure the breathing pattern in real time. Gas or analytes from the desired portions of the breath or from multiple breaths, for example from breath A', B' and C' shown in FIG. 6, are captured and isolated in the storage collection compartments A, B and C. Gas entering the storage compartments is controlled by at least one valve such as the compartment inlet valves for compartments A, B and C using VA1, VB1, and VC1 respectively. For example as shown with Valve VA1 a common port c is always open, and the outlet port is either at "a" to collect and isolate the gas in the storage compartment, or at "b" to bypass the storage compartment. Gas not being captured for analysis is channeled away from the storage compartment via bypass conduits 1000, 2000 and 3000. The captured gas is sent from the storage compartment A, B or C through gas composition analyzers, SA, SB and SC, such as CO sensors, and H2 sensors, NO sensors, and other gas and non-gas sensors. There may be storage compartment outlet valves VA2, VB2 and VC2 which are controlled to further isolate the sample compartments, and valves VA3, VB3 and VC3 between gas analyzers SA, SB and SC and the flow generator 12 that are used to either channel the gas being purged, or drawing the captured samples through the gas analyzers. A control system 22 with a microprocessor 24 controls the system with the associated algorithms and a user interface 30 allows the user to interact with the system. An ambient inlet 32 is provided to purge the system of unwanted gases, or for reference measurements. An inlet valve Vi is provided to control the gas inlet source. The flow generator can be a vacuum or pressure pump, such as a diaphragm pump, or another type of flow generating device such as a vacuum source, a Venturi from a positive pressure source, or a syringe pump. Valves to manage gas routing can be an arrangement of 3 way 2 position valves as shown, or can be an arrangement of 4 way 3 position valves. A capnometer is used measures the breathing pattern instantaneously using infrared (IR). Or and IR sensor can be tuned for other gases or multiple gas types such as O2. Some examples of the gas or analyte composition analyzers are electrochemical sensors with reaction times, gas chromatographers, mass spectrometers, or fast response time sensors such as IR. The sample storage compartment can be a small bore inner diameter tube or conduit of relatively long length in order to reduce the cross section which reduces gas molecule interaction along the length of the conduit. The sampling cannula may be constructed of any non-rigid kink-resistant plastic, such as a thermoset plastic for example silicone, methane or urethane blends, or such as a thermoplastic for example PVC, C-FLEX. Other materials could also be used and the foregoing list should be read to be exemplary and not limiting. The cannula can have a range of inner diameters and in some variations the cannula has a diameter of less than 0.080 inches in order for the breath gas to conform to columnar behavior with definable boundaries between breath sections where mixing across sections may be reduced. In some variations, the inner diameter is between 0.20 inches and 0.50 inches, including 0.25 inches, 0.30 inches, 0.35 inches, 0.40 inches, and 0.45 inches. In other variations, the inner diameter may be different than the foregoing dimensions but configured to prevent mixing of gas. In alternate embodiments, rather than a sampling cannula, a mouthpiece or other conduit can be provided.

As used herein, a sample compartment "prevents mixing" of a gas when the time-sensitive characteristics of the gas are preserved when the gas is stored in the compartment. For example, if a parameter of the gas varies during exhalation, the sample compartment prevents mixing when it preserves the variance in the parameter with respect to the associated timing of the exhalation. In this way, the sampling tube can be considered to retain the gas sections in separate physical locations. However, the term "separate physical locations" is not limited to such sample compartments. As described below, separate physical locations could include separate sampling containers. In this way, a location of a gas portion may be its position within a sampling compartment configured to prevent mixing or the separate sampling container in which it is stored.

FIG. 6 graphically describes a breathing parameter signal versus time t, for example capnometry 50, for a sequence of breaths b1 through b24 being monitored by the system, in accordance with one variation. In this example, the system is looking to capture and analyze normal breaths representative of the patient's normal tidal volume. Breath type threshold values may be established, such as a breathing signal tidal volume peak value 301, and a tidal volume baseline value 302. For example, a normal tidal volume breath may be determined by comparing the actual peak signal amplitude or a breath to the threshold 301, and within a certain percentage, for example 10%, then it may be classified as a normal tidal volume breath. Duration thresholds may also be used to select breaths, such as inspiratory time Ti, breath period time Tbp, expiratory time Te or end-tidal time Tet, shown in breath b13 in the example as 306, 304, 308 and 310 respectively. The thresholds may be determined in advance, or during the test. In the example shown, the patient is breathing somewhat erratically between breaths b2 and b15 in that the breath amplitudes and baselines are inconsistent. Thresholds may be determined for one or more frequency parameters, one or more amplitude parameters and one or more return baseline parameters. If breaths are not meeting these criteria, as determined by Module 3 106 of FIG. 1, they may be dismissed for analysis. In the example shown, the end-tidal samples A', B' and C' of breaths 17, 18 and 19, meet the criteria set by the system and these breaths are then designated as samples that will be analyzed.

Figure 7:
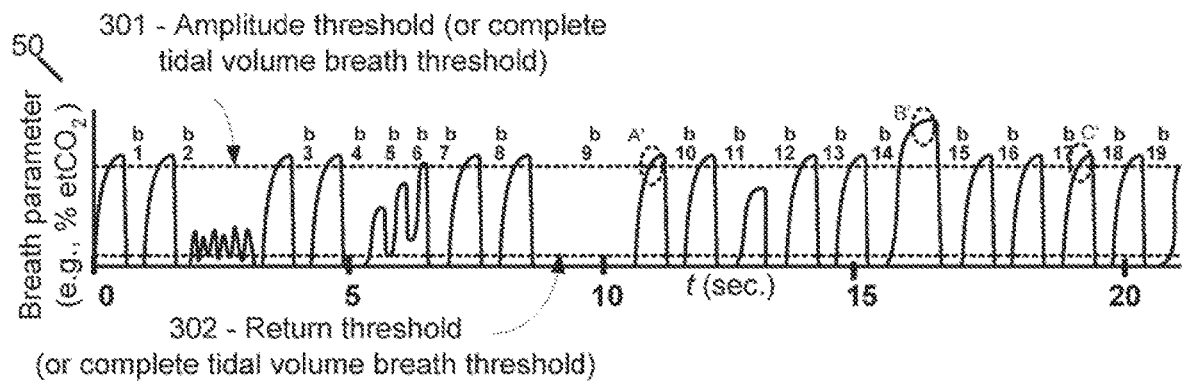
FIG. 7 describes a capnometry plot of another series of breaths that are considered for analysis by the instrument shown in FIG. 5 with three different types of breaths sought, identified, captured and analyzed, in accordance with one variation.

FIG. 7 graphically describes another sequence of breaths b1 through b19 over time, in accordance with one variation. In this series, various artifacts and odd breath types are exemplified. Between breaths b1 and b3, high frequency noise occurs on the breathing signal. Between breaths b3 and b7 breath stacking occurs. Breath b11 is a partial breath, and breath b14 is a larger than normal breath. In this exemplary case, three different analyses are desired: a first analysis in which end tidal gas following an inspiratory hold is desired for that particular analysis, a second analysis in which end tidal gas from a deeper than normal breath is desired for that analysis, and a third analysis in which a normal tidal volume breath in the midst of stead-state breathing conditions is desired for that analysis. Breaths b9, b14 and b17 are selected for these three analyses respectively and samples A', B' and C' from these breaths are captured by the system. The breath registry database contains all the necessary information which is used in the breath analysis module to shuttle the appropriate gas samples to the sample compartments such as A, B and C, and the appropriate sensors SA, SB and SC in FIG. 5.

Figure 8:
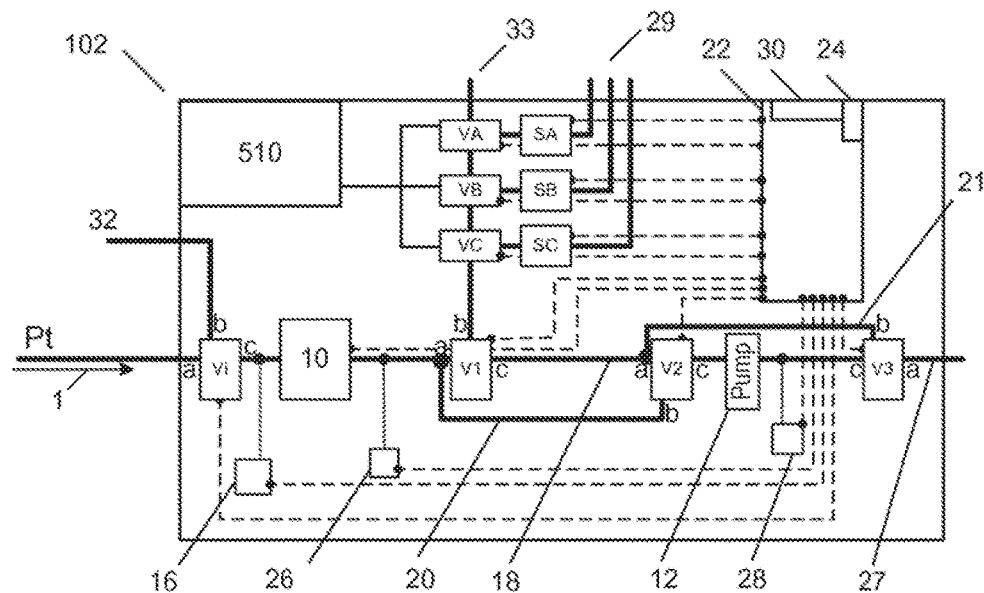
FIG. 8 is a schematic diagram of an alternate exemplary analyzer capable of organizing a registry of gas samples from one or multiple breaths, for example for analyzing more than one substance, in accordance with one variation.

FIG. 8 is a system diagram of a version of breath sample analysis registry system 102 with one sample tube and multiple sensors, in accordance with one variation. The system includes one sample tube 18 used to collect the sample or samples, a sensor array of more than one sensor and/or different types of sensors, SA, SB, SC, a bypass tube 20 to allow unwanted gas to bypass the gas in the sample tube, and a push tube 21 to push the sample to the appropriate sensor. Gas from the patient is drawn in by a cannula 1, or by another type of conduit, and ambient air is drawn in through conduit 32 for system purging or reference measurements. An inert gas reservoir 510 may be included to separate gas samples or for reference measurements. A calibration gas or substance, not shown, may also be included. An additional sensor 26 may be included to measure the gas flow rate, or as a redundant breathing signal sensor. Unneeded gas may be exhausted out of port 33, and analyzed gas may be exhausted out of ports 29. In this example, gas from various breaths, or particular sections of various breaths, or various sections of one or more breaths, is captured in the sample tube. The location of each sample within the sample tube is known from the signal of the breathing pattern sensor 10 and optionally sensor 26, the flow speed of the gas throughout the system, and system timing details. After review of the breath registry information, the system decides what samples to analyze, and knowing exactly where these samples are located, is able to shuttle the samples to the desired sensor.

Figure 9:
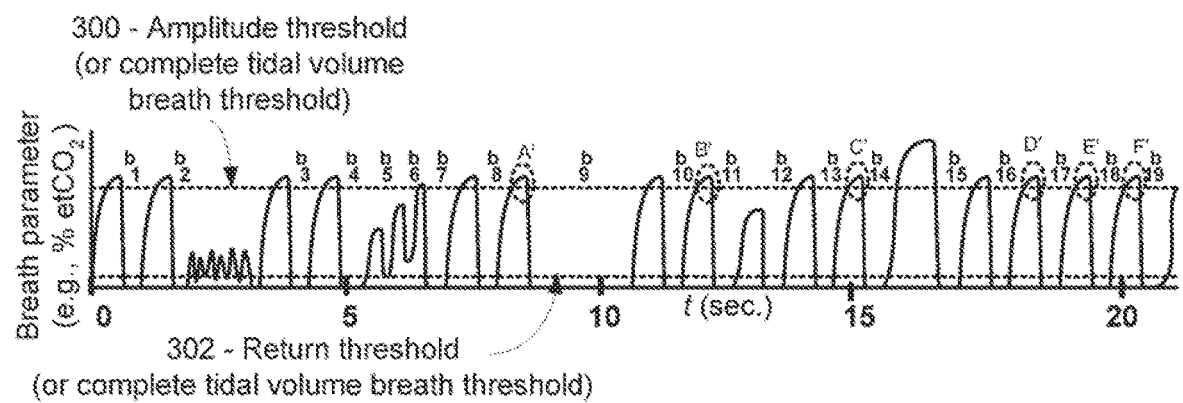
FIG. 9 describes a capnometry plot of a series of breaths that are considered for analysis by the instrument shown in FIG. 8, with a certain breath type sought, identified, captured and analyzed, in accordance with one variation.

FIG. 9 graphically describes a series of breaths b1 through b19 over time, based on a breath signal parameter such as capnometry, in accordance with one variation. If, for example, the system described in FIG. 8 is selected to analyze three different substrates in the end-tidal gas in normal tidal volume breaths, the sample capture algorithms collect the end-tidal samples A', B', C', D', E', and F' of breaths b8, b10, b13, b16, b17 and b18 and shuttle the collected samples to the individual sensors.

Figure 10A:
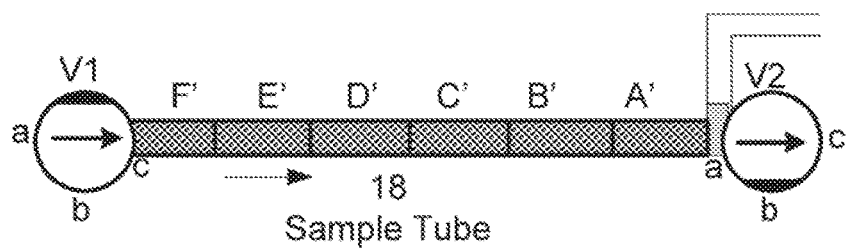
FIG. 10a describes a pneumatic schematic of the sample collection part of the analyzer described in FIG. 8, in which the end-tidal sections of multiple breaths are stored in the sample compartment, in accordance with one variation.
Figure 10B:
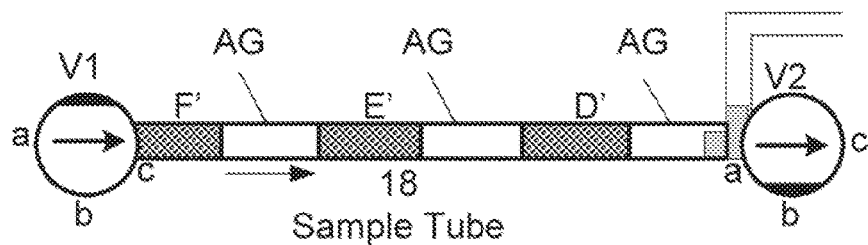
FIG. 10b describes a pneumatic schematic of the sample collection part of the analyzer described in FIG. 8, in which the end-tidal sections of multiple breaths are stored in the sample compartment and are separated by inert or non-end-tidal gas, in accordance with one variation.

FIG. 10a describes a pneumatic schematic of the sample tube 18 shown in FIG. 8, considering the series of breaths shown in FIG. 9, in accordance with one variation. The end-tidal samples A', B', C', D', E' and F' are captured in the sample tube, with their locations known. Then, for example, samples A' and B' are shuttled to sensor SA for a first substance analysis, samples C' and D' are shuttled to sensor SB for a second substance analysis, and samples E' and F' are shuttled to sensor SC for a third substance analysis. While three analyses, two end-tidal samples per analysis, and normal tidal volume breaths are described in this example, they are exemplary only and any number of analyses, and number of samples per analysis and any section of breath, and any type of breath is contemplated. FIG. 10b describes an alternative to the example in FIG. 10a, in which a gas AG, such as an inert gas like N2, or a gas without the substance undergoing analysis, such as ambient air, is inserted into the sample tube in between samples, in order to help keep the samples separate, in accordance with one variation. This optional variation can be employed through the alternative systems shown throughout this specification.

Figure 11:
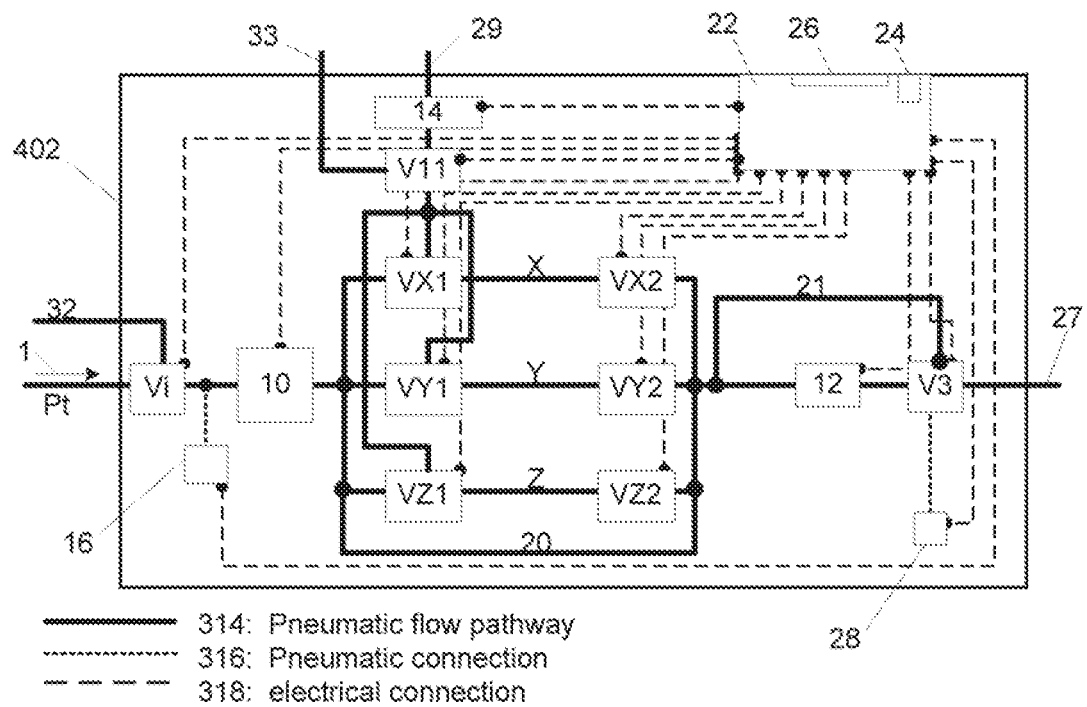
FIG. 11 is a schematic diagram of an alternate exemplary analyzer capable of organizing a registry of gas samples from one or multiple breaths in separate sample compartments, for example for choosing the most optimal sample for analysis, or comparison of the different samples, in accordance with one variation.

FIG. 11 is a schematic of an alternate breath analysis registry system 402 consisting of multiple sample tubes X, Y and Z, and one gas composition sensor 14, in accordance with one variation. Gas from different breaths, or from different portions of one or more breaths, are captured into the sample tubes X, Y and Z. The constituent gas sections in each sample tube are known. The samples in the sample tubes are isolated by inlet and outlet valves VX1, VY1, VZ1, VX2, VY2 and VZ2 respectively. The inlet to the composition sensor 14 is controlled by valve V11 which may exhaust unwanted gas through port 33 or present gas or analytes to sensor 14. Gas that the system does not want to capture or analyze may bypass the sample tubes through the bypass tube 20. After the samples are captured and isolated, and after the breath type and location information is completely logged into the registry, the samples can be shuttled to the sensor for analysis by switching the valves and pushing the sample with ambient air drawn in through the ambient port 32, through the bypass tube 20, through the pump 12 and through the push tube 21, to propel for example the sample in compartment X to the sensor 14. Each sample in each sample tube can be analyzed by the sensor in a similar manner. The samples can be taken from three similar breaths for comparison and averaging, or from different types of breaths for different diagnostic purposes.

Figure 12:
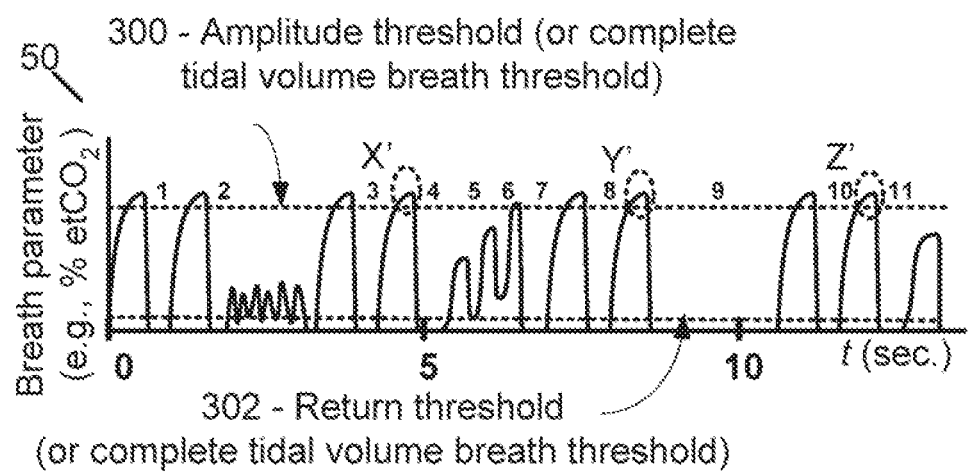
FIG. 12 describes a capnometry plot of a series of breaths that are considered for analysis by the instrument shown in FIG. 11, with a certain breath type sought, identified and captured, and then compared for analysis, in accordance with one variation.

FIG. 12 shows a series of breaths b1 through b11 that is considered for analysis by the system in FIG. 11, in accordance with one variation. In this case, end-tidal gas from three normal breaths are sought for analysis, resulting in capturing samples X', Y' and Z' from breaths b4, b8 and b10, which will be registered in sample compartments X, Y and Z respectively in FIG. 11. The system can alternatively be programmed for other sampling and analyses.

Figure 13:
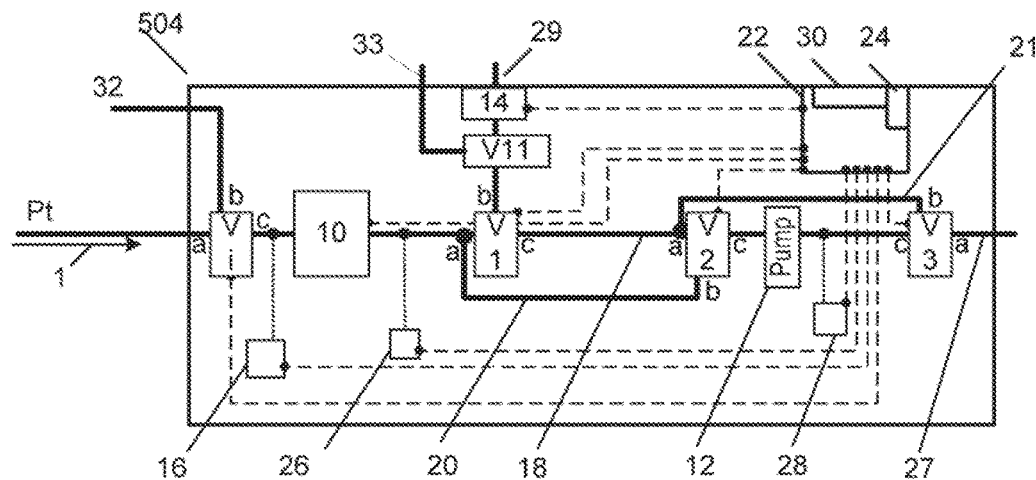
FIG. 13 is a schematic diagram of an alternate exemplary analyzer capable of organizing a registry of gas samples from one or multiple breaths in separate sample compartments, for example for choosing the most optimal portion of the sample for analysis, in accordance with one variation.
Figure 14:
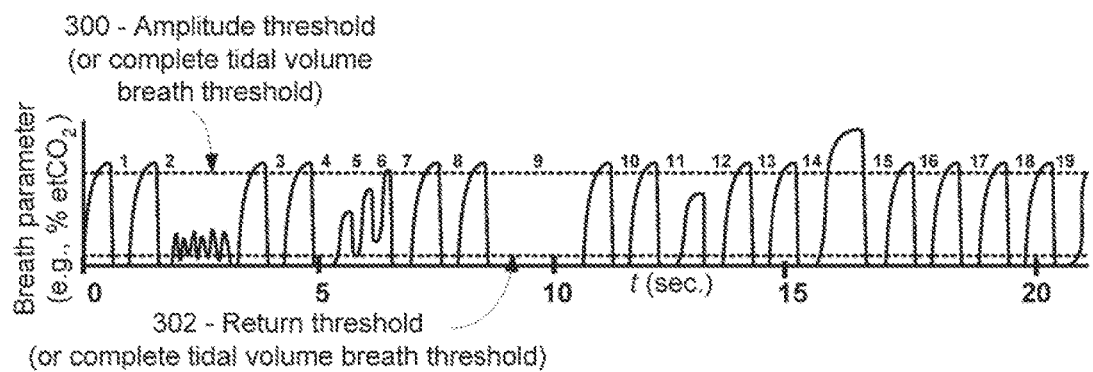
FIG. 14 describes a capnometry plot of a series of breaths that are considered for analysis by the instrument shown in FIG. 13, with a certain breath type sought, identified and located in the sample registry, in accordance with one variation.
Figure 15:
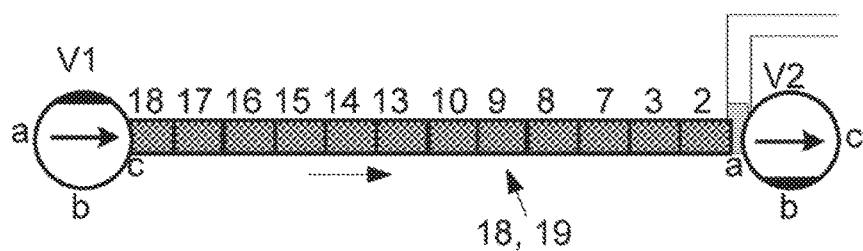
FIG. 15 describes a pneumatic schematic of the sample collection part of the analyzer described in FIG. 13, in which the end-tidal sections of multiple breaths are stored and organized in the sample compartment, in accordance with one variation.
Figure 16:
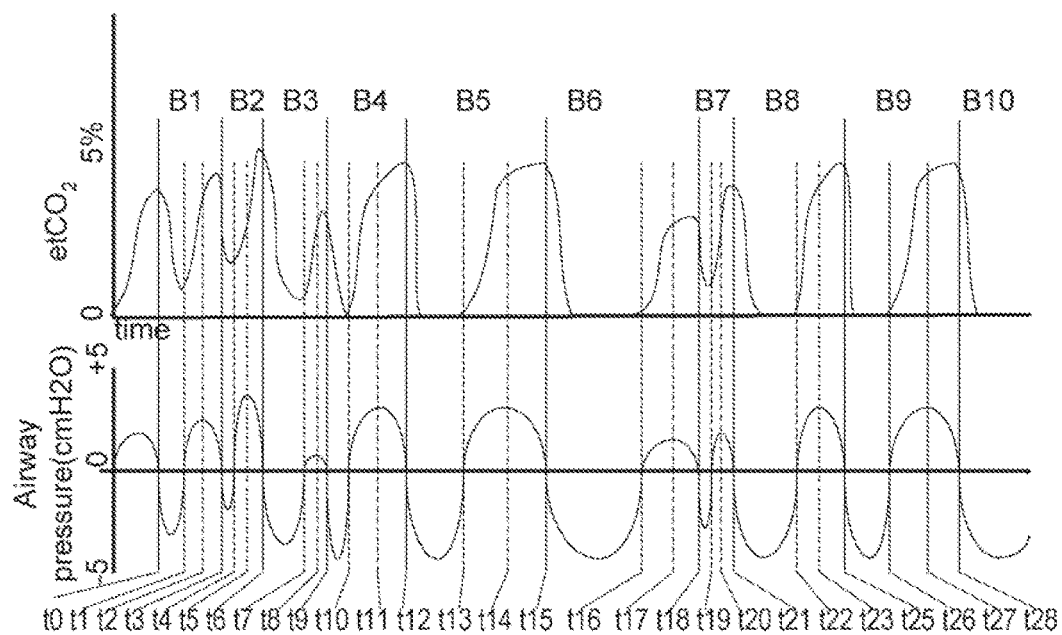
FIG. 16 describes a capnometry plot of a series of breaths that are considered for analysis by the instrument shown in FIG. 13, with breath types, identified and located in the sample registry for subsequent analysis, in accordance with one variation.
Figure 17:
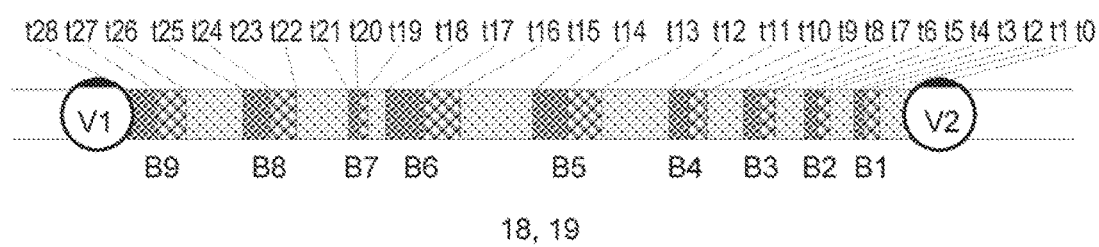
FIG. 17 describes a pneumatic schematic of the sample of the breaths described in FIG. 16, in which multiple breaths including their end-tidal sections are stored and organized in the sample compartment, in accordance with one variation.

FIG. 13 is a schematic of an alternative breath analysis registry system 504 consisting of one sample tube 18 and one compositional sensor 14, in accordance with one variation. Gas from a breath or series of breaths is stored in the sample tube 18. Gas that the system does not want to store bypasses the storage tube through the bypass tube 20 and out the exhaust port 27. As explained previously, the gas stored in the sample tube is characterized in the sample registry in terms of breath type, breath section, and location in the sample tube. In one implementation of this system indicated in FIGS. 14 and 15, end-tidal samples of selected breaths that meet a criterion from a series of breaths are collected in the sample tube, in accordance with one variation. For example, the end-tidal portion of breaths b2, b3, b7, b8, b9, b10, b13, b14, b15, b16, b17 and b18 meet certain initial criteria and are captured in the sample tube 18, creating the registry of samples 19. Other sections of these breaths, and other breaths in their entirety are purged through the system through the bypass tube 20. After analysis of the entire series of breaths, it may for example be decided that the end-tidal sample from breath b18 will be chosen for analysis, and the sample tube gas is pushed by ambient air in the push tube 21 from the ambient inlet 32, the gas that is dismissed for analysis is purged through the system through the purge exhaust port 33, and sample from breath b18 is sent through the composition sensor 14. Alternatively, all of the samples collected in the sample tube can be sent to the sensor 14 for analysis. In another implementation of the system of FIG. 13, all breaths from a series of breaths B1 through B10 can be stored in the sample tube as described in FIGS. 16 and 17. In FIG. 16, the series of breaths is characterized by a capnometry sensor in the top graph, and an airway pressure sensor in the lower graph, such that the type of each breath can be fully and accurately characterized, and so the constituent parts of each breath can be precisely defined as a function of time, and then as a function of location in the sample tube, in accordance with one variation. In FIG. 17 the sample tube of the system of FIG. 13 is shown schematically, in accordance with one variation. As shown in FIG. 17, the location of each breath portion of each breath B9 through B1 may be known in the sample tube based on the available information as previously described. Based on the breath type information in the registry 19, the system algorithms decide on which breath section of which breath will be chosen for analysis, at which time the unwanted gas is purged out of the system through port 33 and the chosen section is shuttled to the gas composition sensor 14. In souse embodiments, additional storage can be provided at the output of the purge port, to allow forward and backward shuffling for subsequent re-sampling.

Figure 18:
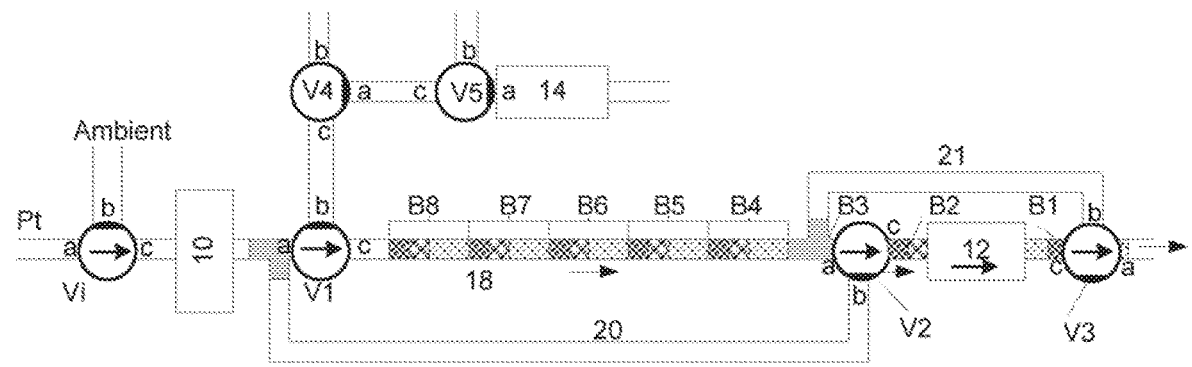
FIG. 18 is a pneumatic schematic describing an example of the breath gas sample collection and segmentation, considering the breath series shown in FIG. 16, in accordance with one variation.
Figure 19:
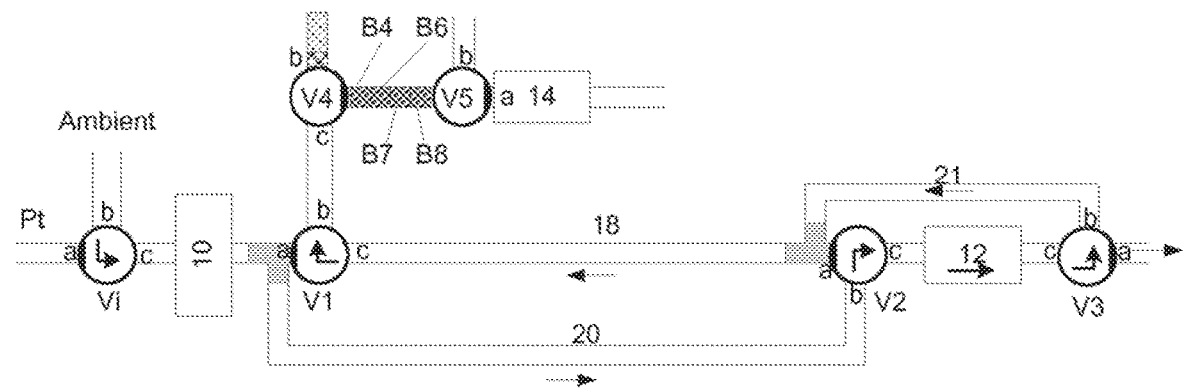
FIG. 19 describes the example in FIG. 18 with chosen sections of chosen breaths shuttled to a secondary storage sample tube where it is staged for subsequent compositional analysis, in accordance with one variation.

FIGS. 18 and 19 describes a variant in which them is a first sample tube and a secondary area for sample staging between valves V4 and V5. In this configuration, multiple sequential breaths can be stored in the primary sample tube 18 as shown in FIG. 18, and then, based on the registry information and system algorithms, the desired sections, such as the end-tidal sections, of various breaths are shuttled by ambient air in the push tube 21 to the secondary staging tube between valves V4 and V5 while the other gas is purged out of the system at port b of valve V4. The gas sections chosen for analysis after being staged in the secondary tube are shown in FIG. 19 and include samples from breaths B4, B6, B7 and B8, which are then shuttled to the composition sensor 14 for analysis. The other sample B5, which is rejected for analysis may be exhausted out of port b of valve V4.

Figure 20:
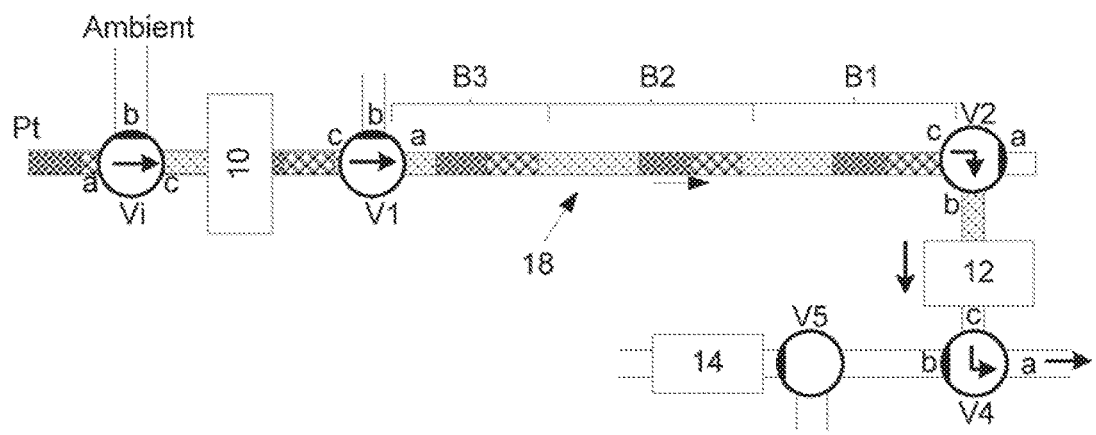
FIG. 20 is a pneumatic schematic describing an example of a system with an in-series sample tube, pump, secondary sample staging tube and compositional sensor, with sections of breath gas organized in the sample tube, considering the breath series shown in FIG. 16, in accordance with one variation.
Figure 21:
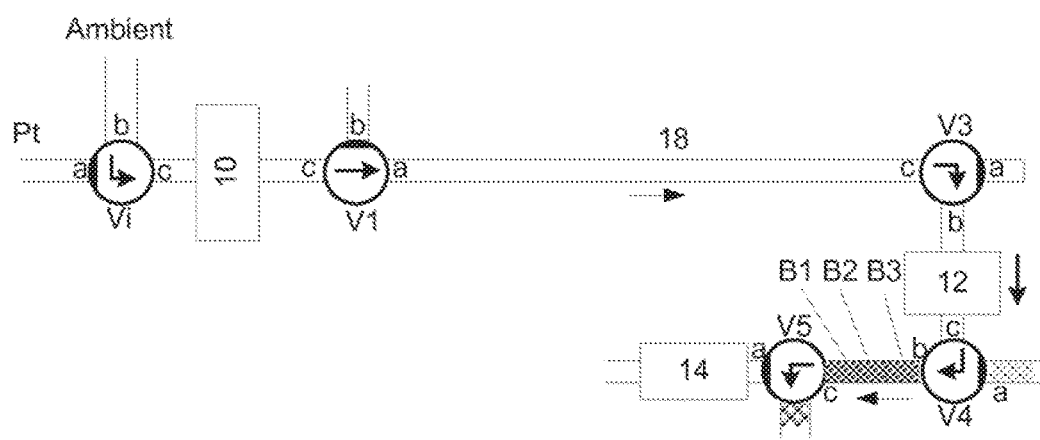
FIG. 21 describes the example in FIG. 20 with chosen sections of chosen breaths shuttled to a secondary sample staging tube where it is staged for subsequent compositional analysis, in accordance with one variation.
Figure 22:
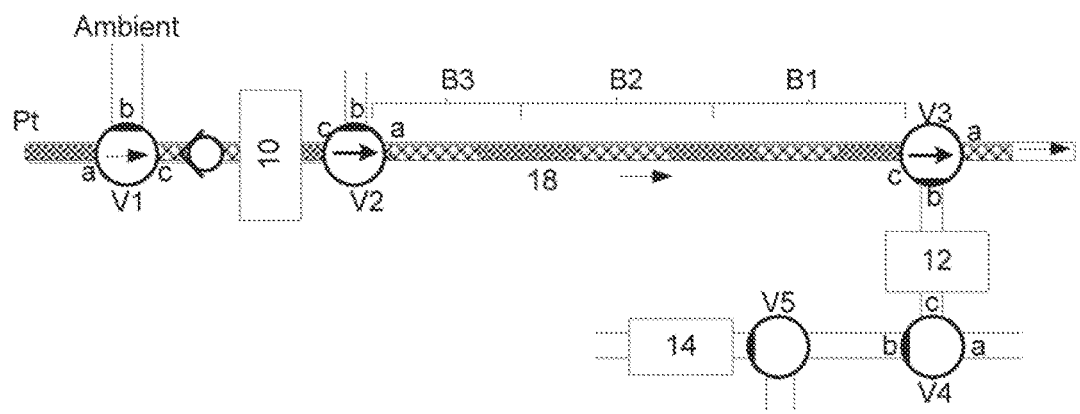
FIG. 22 describes an alternative configuration to the system described in FIG. 20 in which the breath gas is forced into the sample tube by another means, such as from the patient's exhaled flow, and then the sample gas is pumped to the staging tube and/or sensor by use of a pump, in accordance with one variation.

FIGS. 20 and 21 describe a variant in which there is a first sample tube 18 and a secondary tube for sample staging between valves V4 and V5. In this configuration, multiple complete breaths such as a series of sequential breaths can be stored in the primary sample tube as shown in FIG. 20, and then, based on the registry information and system algorithms, the desired sections such as end-tidal sections of various breaths are shuttled by ambient air coming in through valve Vi, out of the sample tube and to the secondary staging tube between valves V4 and V5, while the other gas is purged out of the system at port a of valve V4. The gas sections chosen for analysis after being staged in the secondary tube as shown in FIG. 21 as the end-tidal sections of breaths B1, B2 and B3, are then shuttled to the composition sensor 14 for analysis. While the analyzing the end-tidal sample is again shown in this example, it should be noted that again this is exemplary and the breath section desired to be measured can be anywhere within the breathing cycle, as necessary to measure the most relevant portion of a breath for diagnosing the underlying condition of interest. While the systems in FIGS. 18 and 20 describe the use of a pump to draw the sample from the patient, alternatively as shown in FIG. 22, the breath samples B1, B2 and B3 can be presented into the sample tube 18 via the force of exhalation from the patient pt, in accordance with one variation. Then, after the sample collection and registry routines are performed, a pump 12 can shuttle the gas samples B1, B2 and B3 either out of the purge port a of V4 or to the staging tube between V4 and V5 and ultimately to the sensor 14.

Figure 23:
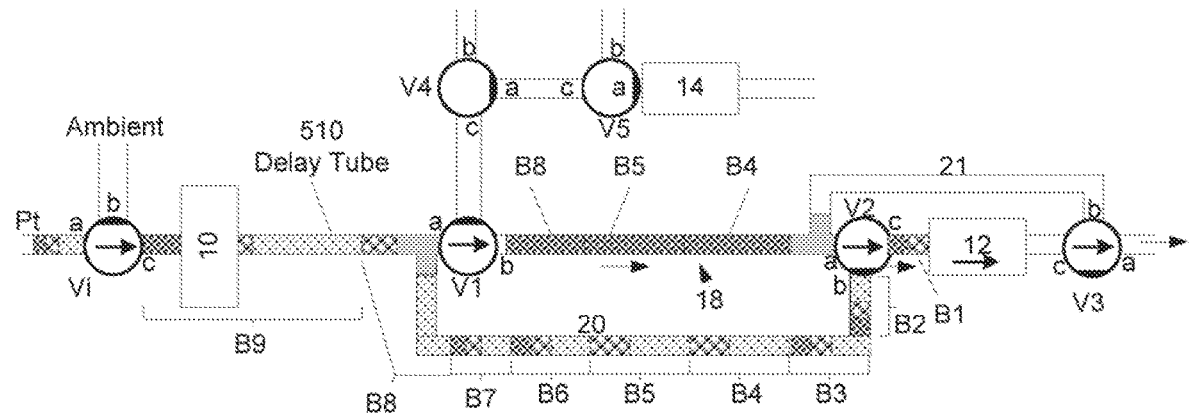
FIG. 23 is a pneumatic schematic describing an alternate configuration of the apparatus with a sample tube, bypass tube, sample push tube, secondary staging tube, and a delay tube to provide time to categorize a breath or breath section to determine if it should be captured or purged, in accordance with one variation.

FIG. 23 describes a variant in which end-tidal gas samples from breaths are routed into the sample tube 18 while other sections of the breaths are rented around the sample tube through the bypass tube 20. Again, based on the registry information and system algorithms, samples that are chosen to be discarded are shuttled by ambient air in the push tube 21, drawn in from Vi, through the purge port b of valve V4, while the chosen sample or samples are shuttled to the secondary tube between V4 and V5, and ultimately to the composition sensor 14. In the example shown, there may be a delay tube 510 positioned between the breathing signal sensor 10 and the sample tube inlet valve V1, such that the system's algorithms has sufficient time to decide whether to collect the breath sample in the sample tube 18, or discard the sample through the bypass tube 20. In the example shown end-tidal samples from breaths B4, B5 and B8 are collected for measurement and the other breaths are discarded.

Figure 24:
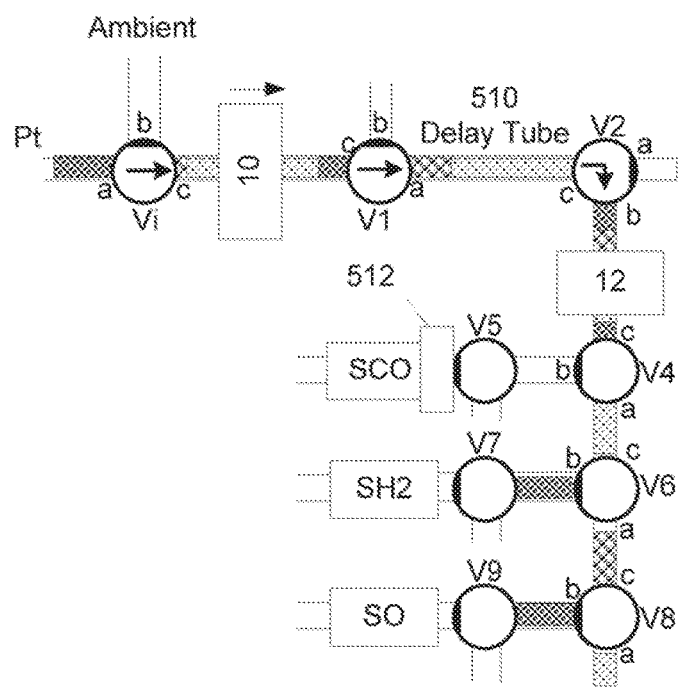
FIG. 24 is a pneumatic schematic describing an alternate configuration of the apparatus with multiple gas composition analyzers and associated sample staging tubes, and with a delay tube to provide time to categorize a breath or breath section to determine if it should be captured or purged, in accordance with one variation.

FIG. 24 describes a variant in which end-tidal samples from selected breaths, based on the breath registry information, are stored in one or more sample tubes while breaths or portions of breaths are purged through port a of valve V8. For example, a breath section will be transferred to the compartment between valves V4 and V5 for CO analysis by sensor SCO, another breath section is transferred to the compartment between valves V6 and V7 for H2 analysis by sensor SH2, and another breath section is transferred to the storage tube between valves V8 and V9 for analysis of some other analyte by sensor SO. Pre-sensor filters 512 may be provided before one or more compositional sensors to filter the gas from an interfering compound prior to compositional analysis. Such filters may filter out aldehydes, alcohols, keytones, hydrogen or other interfering substances. In this example a delay tube 510 is included such that there is sufficient time to analyze the breath type information, and time to query the information in the breath registry, before a decision can be made to discard or keep the sample and to decide which compositional sensor a kept sample should be routed to. Typically the delay tube introduces 1-10 seconds. Alternatively, the delay tube can introduce a delay of up to 60 seconds such that information from many breaths is cataloged in the registry, in this case inside the delay tube 510, before a decision is made to analyze or discard the sample.

Figure 25:
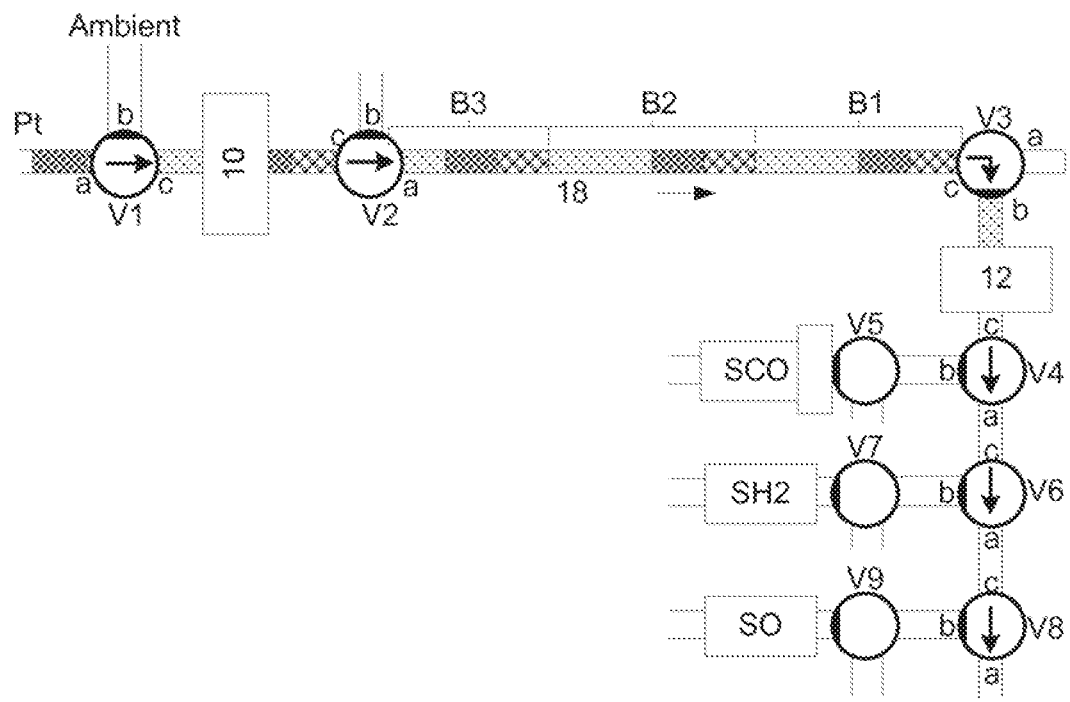
FIG. 25 is a pneumatic schematic describing an example of a system similar to that described in FIG. 20, however with multiple gas composition analyzers and associated secondary storage tubes, in accordance with one variation.
Figure 26:
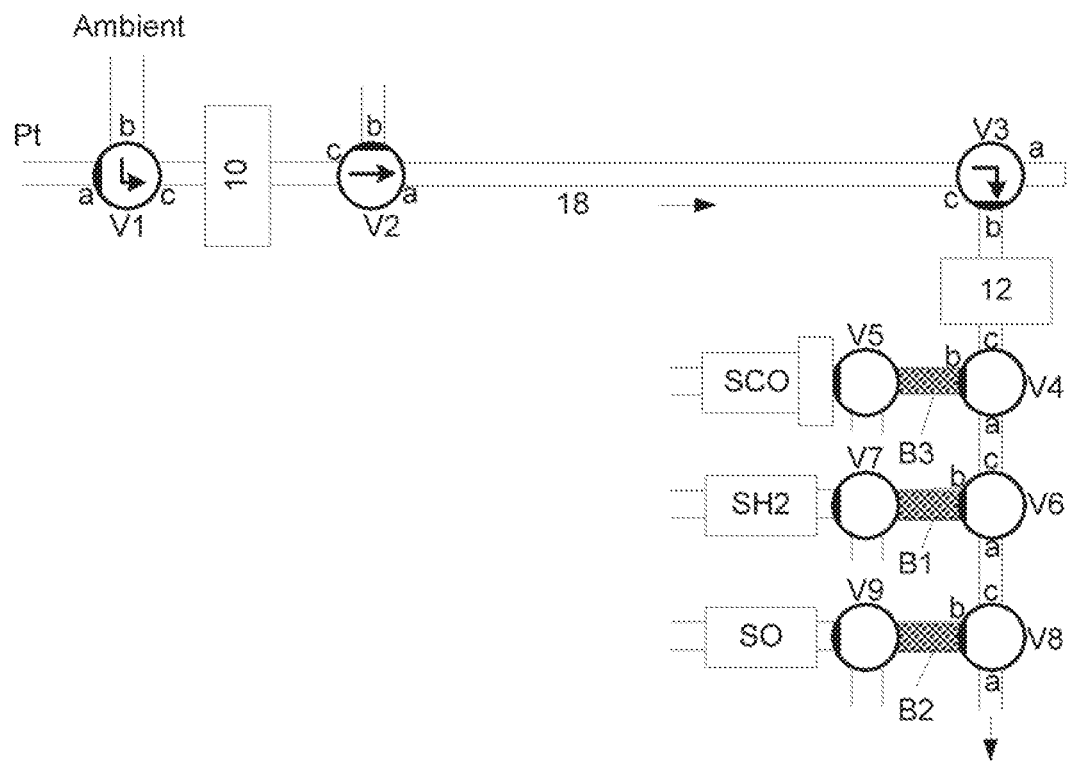
FIG. 26 shows the system described in FIG. 25 with samples transported from the sample tube to the secondary staging tubes, in accordance with one variation.

FIGS. 25 and 26 describes a variant in which gas from a series of multiple breaths are drawn into a sample tube 18 and a sample registry is created, then sections of the breaths, for example the end-tidal sections are shuttled to secondary storage tubes and ultimately to the compositional sensors, while the remaining gas is purged out of port a of valve V8, in accordance with one variation. Specifically, breaths B1, B2 and B3 in their entirety enter the sample tube 18 and are cataloged into the registry. When the system determines the course of action for analysis, the required sections of the selected breaths are shuttled to the sensors SCO, SH2 and SO. The samples may be stored in the secondary storage compartments between valves V4 and V5, V6 and V7, and V8 and V9 if necessary to conduct the compositional analysis, such as would be the case if sections of multiple breaths need to be collected and stored prior to analysis, such as would be the case if a minimum volume was needed, or if averaging over multiple breaths was desired.

Figure 27:
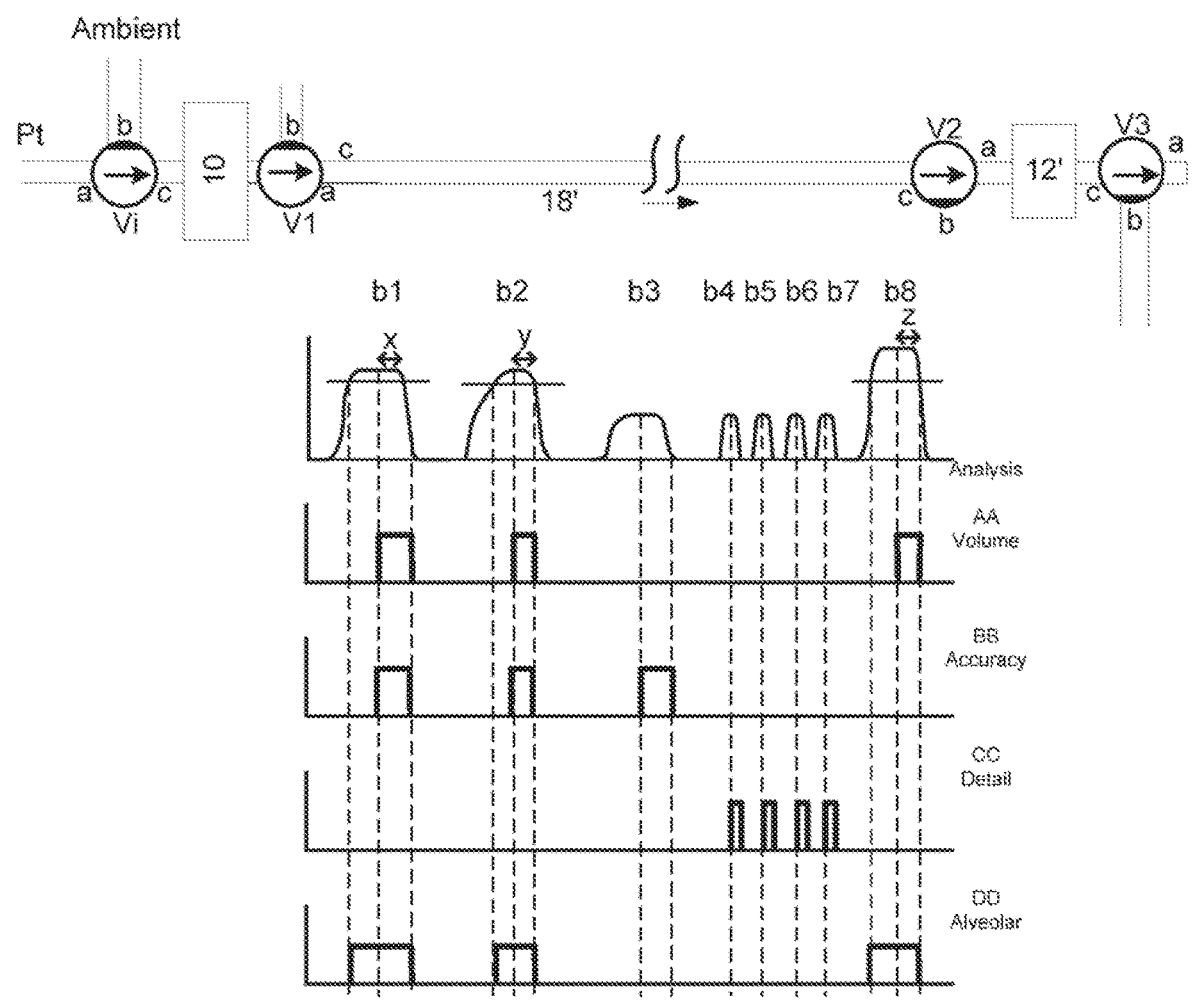
FIG. 27 is a timing diagram of a version of the overall system, showing the timing of different types of breaths superimposed with the sample storage tube, in accordance with one variation.

FIG. 27 shows a variation with the timing tracings of different types of breaths superimposed below a pneumatic schematic of the sample storage tube. This figure shows one implementation of a system with storage volume, three valves and pump, plus a hypothetical series of types of breath waveforms based on CO2 concentration in the top tracing. Similar waveforms can be obtained by measuring instantaneous flow rate, pressure, or by other means. Some information may be stored together with the physical storage of the breath, that allows later identification of breath portions. The composite hypothetical breath comprises eight distinct breath types. Breath b1 (with label x) might represent a normal healthy breath. Breath b2 (with label y) might represent asthma breath, or other breathing disorder. Between breath b2 and breath b3 there may be a short burst of non-breath activity, which may not be considered. Breath b3 has a significantly lower amplitude, which may be a result of dramatically lowered circulation and low breath volume. Breaths b4, b5, b6 and b7 may represent hyperventilation with shallow and fast breathing. Finally, the last breath b8 (with label z), might be a result of the breath following an apnea event, with very different underlying gas concentrations from normal breathing. Exhaled gas can be stored in the storage volume without a pump, or by using a pump. Valve V1 opens the inlet to the storage volume. Valve V2 closes the outlet of the storage volume. The length of the storage volume tube is dependent on the number of breaths that need to be collected for a given clinical paradigm. The volume, inner diameter and length of storage volume without using a pump is limited, and will produce distortion of breath waveforms and increase gas mixing. However, this may be an acceptable loss of accuracy if the sample must be taken where the pump cannot be operated, or if multiple samples must be collected from multiple patients in parallel and analyzed sequentially (as may be the case in a mass emergency situation). The following description includes the pump operating during the sample collection period, but it should be understood that pump operation is not necessarily coupled with sample collection. When the patient breaths into the storage tube, the pump helps draw the exhaled breath into the sample volume. The pump speed can be selected to match the anticipated breath rate, and can be varied in response to changes in breath rate. After the sample is collected, the combination of Valve V3 and pump operation (accompanied by Valve V1 and Valve V2 to allow air or inert gas inlet and flow from storage sample) is used to selectively choose relevant portions of the stored breaths. Valve V3 is a three-way valve, with one outlet connected to an exhaust (or other storage for subsequent analysis), and the second outlet connected to a series of sensors, as described in FIG. 28. A computer driven algorithm may selectively turn Valve V3 from "exhaust" to "analysis" at a rate that would allow sharp segmentation of the underlying stored waveform.

Some examples of analyses are shown in FIG. 27, and will be described as follows. Analysis AA: If one of the main objectives of the measurement is to optimize the volume of end tidal breath to be analyzed (such as in measuring H2 concentration), then relevant sections of the end tidal breath might be grouped together, such as from breaths b1 and b2, labeled x and y. The last section of the hypothetical breath b8 (to the right, labeled z), that may be a result of apnea or another clinical condition, which would not normally be considered in the analysis might need to be included to increase the overall gas volume available for measurment, at the expense of some of the accuracy. The accuracy might be reduced by introducing portion z of the breath, since more than the end-tidal portion is considered, and the breath is not stable with expected concentrations, since it may be an apnea-related breath, with exaggerated CO2 and CO content. Analysis BB: If one of the main objectives of the measurement is to optimize accuracy, then breaths b1, b2 and b3 will be considered, but breath b8 may not, since the first three may have more stable concentrations of gases under investigation. This may be the case when measuring end tidal CO concentration, where parts-per-million accuracy is desired. Any breath conforming to minimal quality criteria would be used, with a shorter portion it, even if its entire end-tidal portion was less than ideal. The algorithm would decide how much of what breath to include in the analysis. Analysis CC: It may be of clinical interest to gauge the severity and residual gas concentrations during a hyperventilation event, especially if such an event is related to a chronic clinical condition. Breaths b4, b5, b6, and b7 would be the only ones recognized and analyzed for this condition. Analysis DD: It may be desired to consider alveolar concentration of gasses when the CO2 reaches a certain threshold, and compare those to other types of measurements for more sophisticated analysis, in which case a "wider" section of breaths b1, b2, and 8 would be ultimately analyzed.

Figure 28:
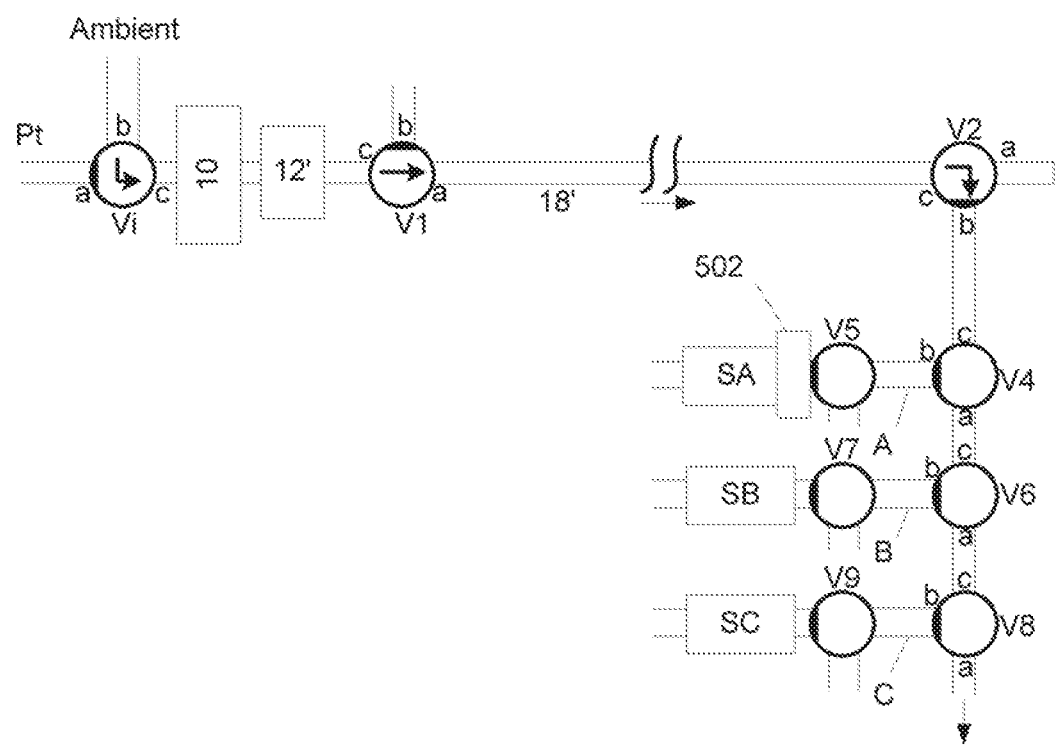
FIG. 28 is a pneumatic schematic describing an alternative configuration to the system described in FIG. 24 in which a pump draws the sample from the patient and propels the sample to various sample tubes and substrate composition sensors, wherein the pump may be a peristaltic type pump so that the organization of the gas constituents in the gas path is not disrupted by the pump, in accordance with one variation.

FIG. 28 is a pneumatic schematic describing an alternative configuration to the system described in FIG. 24 in which a pump 12' draws the sample from the patient Pt and propels the sample to various sample tubes A, B and C, and composition sensors SA, SB and SC, wherein the pump may be a peristaltic type pump so that the organization of the gas constituents in the gas path is not disrupted by the pump, in accordance with one variation. This figure shows one variation of an analysis system, which could include multiple analyte sensing means. Valves 2 and 3, and the pump are the same as in FIG. 27 above. Valves V4, V6 and V8 are connected to separate sample chambers A, B and C respectively, each attached to a specific analyte's sensing means. Each of Sensors SA, SB and SC could be single gas or multiple analyte concentration sensing means. The exhaust at port a of valve V8 could be connected to additional sensing or storage means. The pump could be bi-directional, to allow for two-way movement of storage volume, and incremental analysis. For example, a two-tiered algorithm could be employed to first optimize accuracy, but if not enough gas volume was selected by a particular segments x, y, and z of Breaths 1, 2, and 8, respectively, then additional samples of storage volume gas prior to x, prior to y and prior to z could be added to the sample chamber A and presented to sensor SA. In this case, more volume would be available, but the degree of certainty that only the end-tidal portion was captured would be reduced. Finally, non-linear algorithms involving harmonic analysis, wavelets, and a series of other signal analysis tools could be applied adaptively to the waveform representing the stored breath parameters, to decide which sections of the breath should be analyzed. In systems that provide real time analysis, or analysis of single breath, estimates may be made about stability of the patient, regularity of the breath patterns, etc. With full storage of a number of breaths, the best breaths can be selected after the fact and analyzed, and if necessary, additional breaths, or additional sections of the breaths can be added to the original subsamples to increase accuracy, gas volume, or other parameters to be optimized.

The system in FIGS. 27 and 28 may contain a long capillary tube 18' with one or more valves to store one or more breaths, which can then be retrieved, segment by segment for subsequent, offline chemical analysis. Some implementations may contain a long capillary tube (for single or multiple breath storage), optionally attached operatively to a pump (possibly with reversible flow), one or more valves that route the flow of the exhaled gas to one or more sensors. Additionally, as exhaled gas enters the tube 18' or leaves it, its flow rate, and other fluidic parameters may be measured by flow-through sensors (for flow rate, CO2 concentration, temperature, etc.). Also, the exhaust of the gas at the pump, if used, can also be measured by flow-through sensors.

Some variations of the present disclosure relate to storage, with time markers, of one or more breaths, which may similar to a computer shift register where a breath or breaths are loaded into the storage tube linearly, as exhaled, and detailed timing information is kept for each physical location of the breath, which may include flow rate, pressure, CO2 concentration, etc. Any section of the stored breath(s) can be loaded forward into a set of sensors, including same sections of multiple breaths. For example, if the end tidal concentration of a certain gas is a critical measurement (i.e. hydrogen), it may be necessary to obtain multiple readings of end tidal concentration from multiple breaths, collect them together and then analyze them using a fuel cell sensor. The reason it may be necessary to collect multiple samples is that the fuel cell sensors require a minimum volume of test gas, and also, the fuel cells require significant integration time to reach steady state—possibly several minutes. This may also be true for a number of other sensor types, including mass spectrometry, etc. Additionally, each breath may have a different morphology, especially if the patient has disorderly breathing due to the presence of a disease. In that case, it may be necessary to analyze each breath separately, and select only the end tidal portion (or no portion if the breath is not well defined), to assure that the correct part of the breath is being sampled.

The process may entail collecting one or more breaths into the storage tube, with the timing information being kept separately, and then through engaging a combination of pumps and valves, routing only the relevant portions from one or more breaths to the one or more sensors. Particular attention must be paid to the inner diameter of the capillary tube, to assure that it is sufficiently large to allow for proper inflow of the exhaled gas without turbulent flows and mixing, while also being sufficiently small to prevent gas mixing. This also applies to the selection of the pump speed, which can be either fixed to allow for a range of breaths, or variable to account for breath-to-breath differences, as described in U.S. patent application Ser. No. 13/722,950, assigned to the assignee of the present application, the disclosure of which is incorporated by reference herein in its entirety. Information about pump speeds can be utilized later to "resample" the gasses in the storage tube. The process is very similar to digitally sampling analog signals with a sampling apparatus utilizing adjustable sampling rate. One re-sampling methodology involves using a "chirp" transform, to select the correct sampling points.

Although this disclosure primarily describes variations where the breath storage compartment(s) and the analysis sensor(s) are in the same device, it should be understood that the storage compartment and analysis sensor may be separated. For example, the gas may be field-captured in a compartment configured to prevent mixing. The compartment may or may not be associated with a flow mechanism (such as a vacuum pump, for example) and a mechanism for determining and recording specific portions of the breath (such as a capnometer and software, for example). Then, the stored gas may be transported to a laboratory for the analysis to be performed. The analysis performed may include some or all of the analysis described herein, such as measuring a specific constituent of the breath and/or determining the beginning/end of a specific portion of the breath (such as an end-tidal portion, for example).

Sensors may include fuel cells, MEMS fluidics sensors, optical benches, gas spectrometers, mass spectrometers, and any other type of sensor. Gases analyzed can include any standard gasses traditionally present in exhaled breath, anesthesia gases, unwanted inhaled gases (i.e. poisons, biochemical weapons), or gasses present due to metabolic processes (alcohol, drugs, disease, etc.).

It is also contemplated that new technology on the horizon, such as nanotube sensor technology, may prove to be accurate enough to measure gas composition with the requisite accuracy and in real time. So, while many of the variations describe herein describe a separate breath pattern sensing sensor and step, and a separate gas composition sensor and step, the breath sensing and gas composition analysis steps can be performed by the same sensor, and potentially at the same time. In such apparatuses, the breath information registry variations described here may be beneficial.

As used herein, the term end-tidal typically can be understood to refer to a section of the exhaled breath that is at or near the end of the expiratory period, and typically may be after the deadspace has been exhaled from the person. In addition to measuring gases such as CO in the end-tidal gas exemplified throughout the specification, it is also contemplated that non-gases such as particulates and other chemicals may be measured in the same manner.

In the foregoing descriptions of variations of the invention, it should be noted that it is also conceived that the sequences of operation described in the Figures can be combined in all possible permutations. In addition, while the examples describe ETCO measurement they may apply to other gases, for example hydrogen. The examples provided throughout are illustrative of the principles of the invention, and that various modifications, alterations, and combinations can be made by those skilled in the art without departing from the scope and spirit of the invention. Any of the variations of the various breath measurement and sampling devices disclosed herein can include features described by any other breath measurement and sampling devices or combination of breath measurement and sampling devices herein. Accordingly, it is not intended that the invention be limited, except as by the appended claims. For all of the variations described above, the steps of the methods need not be performed sequentially.

The invention claimed is:
1. A breath sampling apparatus comprising:
a sensor that identifies the beginning and end of a breath, thereby dividing the breath pattern into different breath portions identifying the beginning and end of different breath portions;
a sample tube comprising a capillary channel in which the different breath portions occupy sections of volume of the capillary channel, wherein the sections have at least one end, and wherein the at least one end of adjacent sections are directly coupled to each other by contacting an end of another adjacent section;
a vacuum pump that draws a gas sample from a person's breath into the sample tube, the sample tube comprising gas from at least one breath and at least one breath portion; and
a computer to identify the location of gas in the sample tube corresponding to the beginning and end of the breath, and corresponding to the beginning and end of the breath portion.

2. The breath sampling apparatus of claim 1, further comprising an analyzer that analyzes the different breath portions for a first parameter.

3. The breath sampling apparatus of claim 1, wherein the different breath portions are from a single breath.

4. The breath sampling apparatus of claim 1, wherein the different breath portions are from different breaths.

5. The breath sampling apparatus of claim 2, wherein the analyzer analyzes the different breath portions for a second parameter.

6. The breath sampling apparatus of claim 1, wherein the computer comprises a processor that identifies a desired breath portion from the different breath portions by receiving measurements of a breathing pattern characteristic, and wherein the sample tube receives gas from the desired breath portion.

* * * * *